US007091047B2

(12) United States Patent
Serrero

(10) Patent No.: US 7,091,047 B2
(45) Date of Patent: *Aug. 15, 2006

(54) METHODS AND KITS FOR DIAGNOSING TUMORIGENICITY

(75) Inventor: Ginette Serrero, Ellicott City, MD (US)

(73) Assignee: A&G Pharmaceutical, Inc., Columbia, MD (US)

( * ) Notice: Subject to any disclaimer, the term of this patent is extended or adjusted under 35 U.S.C. 154(b) by 436 days.

This patent is subject to a terminal disclaimer.

(21) Appl. No.: 10/281,160

(22) Filed: Oct. 28, 2002

(65) Prior Publication Data
US 2003/0108950 A1 Jun. 12, 2003

Related U.S. Application Data

(60) Continuation-in-part of application No. 09/456,886, filed on Dec. 8, 1999, now Pat. No. 6,720,159, which is a division of application No. 08/991,862, filed on Dec. 16, 1997, now Pat. No. 6,309,826, which is a continuation-in-part of application No. 08/863,079, filed on May 23, 1997, now abandoned.

(51) Int. Cl.
G01N 33/43 (2006.01)
G01N 33/543 (2006.01)
G01N 33/577 (2006.01)

(52) U.S. Cl. ...................... 436/501; 436/518; 435/7.23

(58) Field of Classification Search ................. 435/7.1, 435/7.23, 501
See application file for complete search history.

(56) References Cited

U.S. PATENT DOCUMENTS

| 5,416,192 | A | 5/1995 | Shoyab et al. |
| 6,309,826 | B1 | 10/2001 | Serrero |
| 6,511,986 | B1 | 1/2003 | Zhang et al. |

FOREIGN PATENT DOCUMENTS

| WO | WO 91/15510 | 10/1991 |
| WO | WO 93/15195 | 8/1993 |

OTHER PUBLICATIONS

Runqing Lu, et al.—"Inhibition of PC cell-derived growth factor (PCDGF, epithelin/granulin precursor) expression by antisense PCDGF cDNA transfection inhibits tumorigenicity of the human breast carcinoma cell line MDA-MB-468," PNAS, vol. 97, No. 8, Apr. 11, 2000, pp. 3993-3998.

Vijay Bhandari, et al.—"Isolation and sequence of the granulin precursor cDNA from human bone marrow reveals tandem cysteine-rich granulin domains," Proc. Natl. Acad. Sci. USA, vol. 89, Mar. 1992, pp. 1715-1719.

Zhiheng He, et al.—"Progranulin Gene Expression Regulates Epithelial Cell Growth and Promotes Tumor Growth in Vivo[1]." Can Cer Research 59, Jul. 1, 1999, pp. 3222-3229.

International Search Report dated May 13, 2003.

Effect of Testosterone on the Growth Properties and on Epidermal Growth Factor Receptor Expression in the Teratoma-derived Tumorigenic Cell Line 1246-3A, Serrero, G. et al., Cancer Research 52, 1992, pp. 4242-4247.

Molecular Biology of the Cell, Alberts, B., et al., Garland Publishing, Inc., 1983.

Growth Factors in Development, Transformation, and Tumorigenesis, Cross, M. et al., Cell, vol. 64, 1991, pp. 271-280.

Autocrine Secretion and Malignant Transformation of Cells, Sporn, M.B. et al., The New England Journal of Medicine, vol. 303, 1980, pp. 878-880.

Purification of an Autocrine Growth Factor Homologous with Mouse Epithelin Precursor from a Highly Tumorigenic Cell Line, Zhou, J. et al., The Journal of Biological Chemistry, vol. 268, No. 15, 1993, pp. 10863-10869.

The Epithelin Precursor Encodes Two Proteins with Opposing Activities on Epithelial Cell Growth, Plowman, G. et al., The Journal of Biological Chemistry, vol. 267, No. 18, 1992, pp. 13073-13078.

Granulins, a Novel Class of Peptide from Leukocytes, Bateman, A. et al., Biochemical and Biophysical Research Communications, vol. 173, No. 3, 1990, pp. 1161-1168.

A Synthetic Fragment of Rat Transforming Growth Factor with Receptor Binding and Antigenic Properties, Nestor, J. et al., Biochemical and Biophysical Research Communications, vol. 129, No. 1, 1985, pp. 226-232.

In Vitro Deletional Mutagenesis for Bacterial Production of the 20,000-Dalton Form of Human Pituitary Growth Hormone, Adelman, J. et al., DNA, vol. 2, No. 3, 1983, pp. 183-193.

An In Vitro Model to Study Adipose Differentiation in Serum-Free Medium, Serrero, G. et al., Analytical Biochemistry 120, 1982, pp. 351-359.

Study of a Teratoma-Derived Adipogenic Cell Line 1246 and Isolation of an Insulin-Independent Variant in Serum-Free Medium, Serrero-Dave, G., Cancer Center, University of California, pp. 366-376.

(Continued)

Primary Examiner—Misook Yu
(74) Attorney, Agent, or Firm—Dickstein Shapiro Morin & Oshinsky LLP

(57) ABSTRACT

Methods and kits for diagnosing tumorigenicity by measuring the concentration of GP88 in blood, plasma, serum, saliva, urine and other biological fluids. The methods and kits detect GP88 in biological fluids at a concentration as low as about 0.1 to 10 nanograms per milliliter and are useful for determining whether a patient has a tumorigenic condition, whether the patient is likely to be responsive to anti-tumorigenic therapies, and whether the treated patient is responding to anti-tumorigenic therapy by measuring the concentration of GP88 in the patient's serum or other biological fluid.

37 Claims, 20 Drawing Sheets

OTHER PUBLICATIONS

*Tumorigenicity Associated with Loss of Differentiation and of Response to Insulin in the Adipogenic Cell Line 1246*, Serrero, G., In Vitro Cellular & Developmental Biology, vol. 21, No. 9, 1985, pp. 537-540.

*Decreased Transforming Growth Factor-β Response and Binding in Insulin-independent Teratoma-Derived Cell Lines with Increased Tumorigenic Properties*, Serrero, G. et al., Journal of Cellular Physiology, 149, 1991, pp. 503-511.

*Growth Inhibition of Human Breast Cancer Cells in Vitro with an Antibody against the Type I Somatomedin Receptor*, Arteaga, C. et al., Cancer Research 49, 1989, pp. 6237-6241.

*The Biological Effects of a High Molecular Weight Form of IGF II in a Pluripotential Human Teratocarcinoma Cell Line*, Schofield, P. et al., Anticancer Research 14, 1994, pp. 533-538.

*Gene therapy of murine teratocarcinoma: Separate functions for insulin-like growth factors I and II in immunogenicity and differentiation*, Trojan, J. et al., Proc. Natl. Acad. Sci. USA, vol. 91, 1994, pp. 6088-6092.

*Treatment and Prevention of Rat Glioblastoma by Immunogenic C6 Cells Expressing Antisense Insulin-Like Growth Factor I RNA*, Trojan, J. et al., Science, vol. 259, 1993, pp. 94-96.

*Continuous cultures of fused cells secreting antibody of predefined specificity*, Kohler, G. et al., Nature, vol. 256, 1975, pp. 495-497.

*Production of Monoclonal Antibodies: Strategy and Tactics*, de St. Groth, S.F. et al., Journal of Immunology Methods, 35, 1980, pp. 1-21.

*Hybridoma Techniques*, Schreier, M. et al., Cold Spring Harbor Laboratory, 1980.

*Generation of antibody activity from immunoglobulin polypeptide chains produced in Escherichia coli*, Cabilly, S. et al., Proc. Natl. Acad. Sci. USA, vol. 81, 1984, pp. 3273-3277.

*Chimeric human antibody molecules: Mouse antigen-binding domains with human constant region domains*, Morrison, S. et al., Proc. Natl. Acad. Sci. USA, vol. 81, 1984, pp. 6851-6855.

*Chimeric mouse-human IgG1 antibody that can mediate lysis of cancer cells*, Liu, A. et al., Proc. Natl. Acad. Sci. USA, vol. 84, 1987, pp. 3439-3443.

*Escherichia coli Secretion of an Active Chimeric Antibody Fragment*, Better, M. et al., Science, vol. 240, 1988, pp. 1041-1043.

*Reshaping human antibodies for therapy*, Riechmann, L. et al., Nature, vol. 332, 1988, pp. 323-327.

*Antibody Humanization Using Monovalent Phage Display*, Baca, M. et al., J. Biol. Chem., vol. 272, No. 16, 1997, pp. 10678-10684.

*A Combinatorial Library Strategy for the Rapid Humanization of Anticarcinoma BR96 Fab*, Rosok, M.J. et al., J. Biol. Chem., vol. 271, No. 37, 1996, pp. 22611-22618.

*Improved Radioimaging and Tumor Localization with Monoclonal F(ab')*, Wahl, R.L. et al., The Journal of Nuclear Medicine, vol. 24, No. 4, 1983, pp. 316-325.

*Clinical Use of a Monoclonal Antibody to Bombesin-lik Peptide in Patients with Lung Cancer*, Mulshine, J.L., Annals New York Academy of Sciences, pp. 360-372.

*Antisense RNA inhibits splicing of pre-mRNA in vitro*, Munroe, S.H., The EMBO Journal, vol. 7, No. 8, 1988, pp. 2523-2532.

*Specific Synthesis of DNA in vitro via a Polymerase-Catalyzed Chain Reaction*, Mulis, K.B. et al., Methods in Enzymology, vol. 155, 1987, pp. 335-350.

*Antisense approaches to cancer gene therapy*, Mercola, D. et al., Cancer Gene Therapy, vol. 2, No. 1, 1995, pp. 47-59.

*Gene inhibition using antisense oligodeoxynucleotides*, Wagner, R. W., Nature, vol. 372, 1994, pp. 333-335.

*Molecular Cloning: A Laboratory Manual*, Maniatis, T. et al., Cold Spring Harbor Laboratory, 1982.

*Design and Application of Antisense Oligonucleotides in Cell Culture, in Vivo, and as Therapeutic Agents*, Brysch, W. et al., Cellular and Molecular Neurobiology, vol. 14, No. 5, 1994, pp. 557-568.

*Rational Design of Sequence-specific Oncogene Inhibitors Based on Antisense and Antigene Oligonucleotides*, Helene, C., Eur. J. Cancer, vol. 27, No. 11, 1991, pp. 1466-1471.

*Optimization of Antisense Oligodeoxynucleotide Structure for Targeting ber-abl mRNA*, Giles, R.V. et al., Blood, vol. 86, No. 2, 1995, pp. 744-754.

*Extending the chemistry that supports genetic information transfer in vivo: Phosphorothioate DNA, phosphorothioate RNA, 2'-O-methyl RNA, and methylphosphonate DNA*, Thaler, D.S. et al., Proc. Natl. Acad. Sci. USA, vol. 93, 1996, pp. 1352-1356.

*Oligonucleotides N3'-P5' phosphoramidates as antisense agents*, Gryaznov, S. et al., Nucleic Acids Research, vol. 24, No. 8, 1996, pp. 1508-1514.

*Cationic liposomes improve stability and intracellular delivery of antisense oligonucleotides into CaSki cells*, Lappalainen, K. et al., Biochimica et Biophysica Acta 1196, 1994, pp. 201-208.

*Block of AIDS-Kaposi's Sarcoma (KS) Cell Growth, Angiogenesis, and Lesion Formation in Nude Mice by Antisense Oligonucleotide Targeting Basic Fibroblast Growth Factor*, Ensoli, B. et al., The Journal of Clinical Investigation, Inc., vol. 94, 1994, pp. 1736-1746.

*Growth Inhibition of Malignant CD5+B (B-1) Cells by Antisense IL-10 Oligonucleotide*, Peng, B. et al., Leukemia Research, vol. 19, No. 3, 1995, pp. 159-167.

*Review: Optimizing inducer and culture conditions for expression of foreign proteins under the control of the lac promoter*, Donovan, R.S. et al., Journal of Industrial Microbiology, 16, 1996, pp. 145-154.

*Prokaryotic gene expression in vitro: Transcription-translation coupled systems*, Cenatiempo, Y., Biochimie, 68, 1986, pp. 505-515.

*Bacterial Regulation: Global Regulatory Networks*, Gottesman, S., Ann, Rev. Genet., 18, 1984, pp. 415-441.

*Regulation In Vivo of a Cloned Mammalian Gene: Cadmium Induces the Transcription of a Mouse Metallothionein Gene in SV40 Vectors*, Hamer, D.H. et al., Journal of Molecular and Applied Genetics, vol. 1, No. 4, 1982, pp. 273-288.

*Functional Relationships between Transcriptional Control Signals of the Thymidine Kinase Gene of Herpes Simplex Virus*, McKnight, S.L., Cell, vol. 31, 1982, pp. 355-365.

*Isolation of the yeast regulatory gene GAL4 and analysis of its dosage effects on the galactose/melibiose regulon*, Johnston, S.A. et al., Proc. Natl. Acad. Sci. USA, 79, 1982, pp. 6971-6975.

*In vivo sequence requirements of the SV40 early promoter region*, Benoist, C. et al., Nature, vol. 290, 1981, pp. 304-310.

*Cloning, Structure, and Expression of the Mitochondrial Cytochrome P-450 Sterol 26-Hydroxylase, a Bile Acid Biosynthetic Enzyme*, Andersson, S. et al., The Journal of Biological Chemistry, vol. 264, No. 14, 1989, pp. 8222-8229.

*Insulin and Insulin-like Growth Factor Signaling Are Defective in the MDA MB-468 Human Breast Cancer Cell Line*, Sepp-Lorenzino, L. et al., Cell Growth & Differentiation, vol. 5, 1994, pp. 1077-1083.

*Biochemical Analysis of the Epithelin Receptor*, Culouscou, J.M. et al., The Journal of Biological Chemistry, vol. 268, No. 14, 1993, pp. 10458-10462.

*Targeted Toxins as Anticancer Agents*, Siegall, C.B., Cancer, vol. 74, No. 3, 1994, pp. 1006-1012.

Zhang, Haidi—"Overexpression of PC Cell Derived Growth Factor (PCDGF) Contributes To The Highly Tumorigenic Properties Of Producer Cell Line PC" a Dissertation submitted in partial fulfillment of the requirements for the degree of Doctor of Philosophy, Chemistry, Fall of 1997, 143 pages, Clarkson University.

Vijay Bandhari and Andrew Bateman, "Structure and Chromosmal Location of the human granulin gene," Biochemical and Biophysical Research Communications, vol. 188, No. 1, 1992, pp. 57-63, XP001018991, abstract, figure 2.

Bhandari et al., "The Complementary Deoxyribonucleic Acid Sequence, Tissue Distribution, and Cellular Localization of the Rat Granulin Precursor," Endocrinology, vol. 133, No. 6, 1993, pp. 2682-2689, XP001021601.

Haidi Zhang and Ginette Serrero, "Inhibition of tumorigenicity of the teratoma PC cell line by transfection with antisense cDNA for PC cell-derived growth factor (PCDGF, epithelin/granulin precursor)," PNAS, vol. 95, Nov. 1998, pp. 14202-14207, XP002177206.

European Search Report dated Oct. 23, 2001.

ABSENCE OF TUMOR FORMATION IN C3H MICE BY INHIBITION OF GP88 EXPRESSION
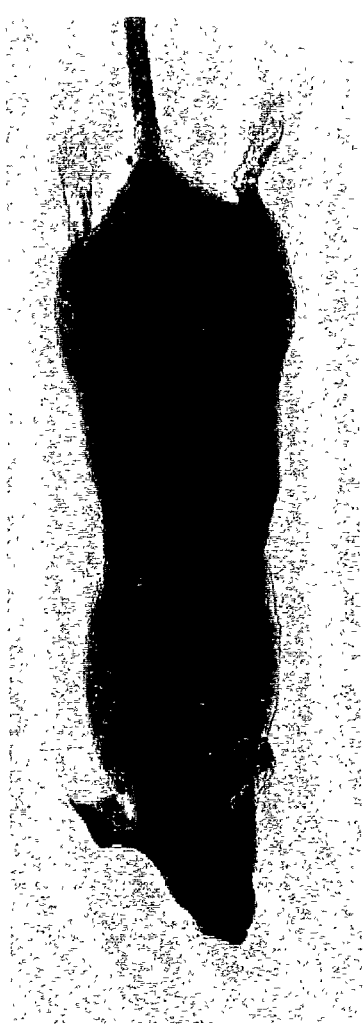
GP88 ANTISENSE TRANSFECTED PC CELLS
CONTROL TRANSFECTED PC CELLS
FIG. 3

GP88 mRNA EXPRESSION IN ESTROGEN-DEPENDENT AND INDEPENDENT HUMAN MAMMARY CARCINOMA CELLS

Mouse GP88 cDNA

```
 C  GGA CCC CGA CGC AGA CAG ACC ATG TGG GTC CTG ATG AGC TGG CTG    46
                                  M   W   V   L   M   S   W   L     8

GCC TTC GCG GCA GGG CTG GTA GCC GGA ACA CAG TGT CCA GAT GGG CAG    94
 A   F   A   A   G   L   V   A   G   T   Q   C   P   D   G   Q    24

TTC TGC CCT GTT GCC TGC TGC CTT GAC CAG GGA GGA GCC AAC TAC AGC   142
 F   C   P   V   A   C   C   L   D   Q   G   G   A   N   Y   S    40

TGC TGT AAC CCT CTT CTG GAC ACA TGG CCT AGA ATA ACG AGC CAT CAT   190
 C   C   N   P   L   L   D   T   W   P   R   I   T   S   H   H    56

CTA GAT GGC TCC TGC CAG ACC CAT GGC CAC TGT CCT GCT GGC TAT TCT   238
 L   D   G   S   C   Q   T   H   G   H   C   P   A   G   Y   S    72

TGT CTT CTC ACT GTG TCT GGG ACT TCC AGC TGC TGC CCG TTC TCT AAG   286
 C   L   L   T   V   S   G   T   S   S   C   C   P   F   S   K    88

GGT GTG TCT TGT GGT GAT GGC TAC CAC TGC TGC CCC CAG GGC TTC CAC   334
 G   V   S   C   G   D   G   Y   H   C   C   P   Q   G   F   H   104

TGT AGT GCA GAT GGG AAA TCC TGC TTC CAG ATG TCA GAT AAC CCC TTG   382
 C   S   A   D   G   K   S   C   F   Q   M   S   D   N   P   L   120

GGT GCT GTC CAG TGT CCT GGG AGC CAG TTT GAA TGT CCT GAC TCT GCC   430
 G   A   V   Q   C   P   G   S   Q   F   E   C   P   D   S   A   136

ACC TGC TGC ATT ATG GTT GAT GGT TCG TGG GGA TGT TGT CCC ATG CCC   478
 T   C   C   I   M   V   D   G   S   W   G   C   C   P   M   P   152

CAG GCC TCT TGC TGT GAA GAC AGA GTG CAT TGC TGT CCC CAT GGG GCC   526
 Q   A   S   C   C   E   D   R   V   H   C   C   P   H   G   A   168

TCC TGT GAC CTG GTT CAC ACA CGA TGC GTT TCA CCC ACG GGC ACC CAC   574
 S   C   D   L   V   H   T   R   C   V   S   P   T   G   T   H   184

ACC CTA CTA AAG AAG TTC CCT GCA CAA AAG ACC AAC AGG GCA GTG TCT   622
 T   L   L   K   K   F   P   A   Q   K   T   N   R   A   V   S   200

TTG CCT TTT TCT GTC GTG TGC CCT GAT GCT AAG ACC CAG TGT CCC GAT   670
 L   P   F   S   V   V   C   P   D   A   K   T   Q   C   P   D   216
```

FIG.8A

Mouse GP88 cDNA (continued)

```
GAT TCT ACC TGC TGT GAG CTA CCC ACT GGG AAG TAT GGC TGC TGT CCA    718
 D   S   T   C   C   E   L   P   T   G   K   Y   G   C   C   P    232

ATG CCC AAT GCC ATC TGC TGT TCC GAC CAC CTG CAC TGC TGC CCC CAG    766
 M   P   N   A   I   C   C   S   D   H   L   H   C   C   P   Q    248

GAC ACT GTA TGT GAC CTG ATC CAG AGT AAG TGC CTA TCC AAG AAC TAC    814
 D   T   V   C   D   L   I   Q   S   K   C   L   S   K   N   Y    264

ACC ACG GAT CTC CTG ACC AAG CTG CCT GGA TAC CCA GTG AAG GAG GTG    862
 T   T   D   L   L   T   K   L   P   G   Y   P   V   K   E   V    280

AAG TGC GAC ATG GAG GTG AGC TGC CCT GAA GGA TAT ACC TGC TGC CGC    910
 K   C   D   M   E   V   S   C   P   E   G   Y   T   C   C   R    296

CTC AAC ACT GGG GCC TGG GGC TGC TGT CCA TTT GCC AAG GCC GTG TGT    958
 L   N   T   G   A   W   G   C   C   P   F   A   K   A   V   C    312

TGT GAG GAT CAC ATT CAT TGC TGC CCG GCA GGG TTT CAG TGT CAC ACA   1006
 C   E   D   H   I   H   C   C   P   A   G   F   Q   C   H   T    328

GAG AAA GGA ACC TGC GAA ATG GGT ATC CTC CAA GTA CCC TGG ATG AAG   1054
 E   K   G   T   C   E   X   G   I   L   Q   V   P   W   M   K̲    344

AAG GTC ATA GCC CCC CTC CGC CTG CCA GAC CCA CAG ATC TTG AAG AGT   1102
 K̲   V̲   I̲   A̲   P̲   L̲   R̲   L̲   P̲   D̲   P̲   Q̲   I̲   L̲   K̲   S̲    360

GAT ACA CCT TGT GAT GAC TTC ACT AGG TGT CCT ACA AAC AAT ACC TGC   1150
 D̲   T̲   P   C   D   D   F   T   R   C   P   T   N   N   T   C    376

TGC AAA CTC AAT TCT GGG GAC TGG GGC TGC TGT CCC ATC CCA GAG GCT   1198
 C   K   L   N   S   G   D   W   G   C   C   P   I   P   E   A    392

GTC TGC TGC TCA GAC AAC CAG CAT TGC TGC CCT CAG GGC TTC ACA TGT   1246
 V   C   C   S   D   N   Q   H   C   C   P   Q   G   F   T   C    408

CTG GCT CAG GGG TAC TGT CAG AAG GGA GAC ACA ATG GTG GCT GGC CTG   1294
 L   A   Q   G   Y   C   Q   K   G   D   T   M   V   A   G   L    424

GAG AAG ATA CCT GCC CGC CAG ACA ACC CCG CTC CAA ATT GGA GAT ATC   1342
 E   K   I   P   A   R   Q   T   T   P   L   Q   I   G   D   I    440
```

FIG.8B

Mouse GP88 cDNA (continued)

```
GGT TGT GAC CAG CAT ACC AGC TGC CCA GTA GGG CAA ACC TGC TGC CCA    1390
 G   C   D   Q   H   T   S   C   P   V   G   Q   T   C   C   P     456

AGC CTC AAG GGA AGT TGG GCC TGC TGC CAG CTG CCC CAT GCT GTG TGC    1438
 S   L   K   G   S   W   A   C   C   Q   L   P   H   A   V   C     472

TGT GAG GAC CGG CAG CAC TGT TGC CCG GCC GGG TAC ACC TGC AAC GTG    1486
 C   E   D   R   Q   H   C   C   P   A   G   Y   T   C   N   V     488

AAG GCG AGG ACC TGT GAG AAG GAT GTC GAT TTT ATC CAG CCT CCC GTG    1534
 K   A   R   T   C   E   K   D   V   D   F   I   Q   P   P   V     504

CTC CTG ACC CTC GGC CCT AAG GTT GGG AAT GTG GAG TGT GGA GAA GGG    1582
 L   L   T   L   G   P   K   V   G   N   V   E   C   G   E   G     520

CAT TTC TGC CAT GAT AAC CAG ACC TGT TGT AAA GAC AGT GCA GGA GTC    1630
 H   F   C   H   D   N   Q   T   C   C   K   D   S   A   G   V     536

TGG GCC TGC TGT CCC TAC CTA AAG GGT GTC TGC TGT AGA GAT GGA CGT    1678
 W   A   C   C   P   Y   L   K   G   V   C   C   R   D   G   R     552

CAC TGT TGC CCC GGT GGC TTC CAC TGT TCA GCC AGG GGA ACC AAG TGT    1726
 H   C   C   P   G   G   F   H   C   S   A   R   G   T   K   C     568

TTG CGA AAG AAG ATT CCT CGC TGG GAC ATG TTT TTG AGG GAT CCG GTC    1774
 L   R   K   K   I   P   R   W   D   M   F   L   R   D   P   V     584

CCA ACA CCG CTA CTG TAA GGA AGG GCT ACA GAC TTA AGG AAC TCC ACA    1822
 P   T   P   L   L   *                                              589

GTC CTG GGA ACC TGT TTC CGA GGG TAC CCA CTA CTC AGG CCT CCC TAG    1870
CGC CTC CTC CCC TAA CGT CTC CCC GGC CTA CTC ATC CTG AGT CAC CCT    1918
ATC ACC ATG GGA GGT GGA GCC TCA AAC TAA AAC CTT CTT TTA TGG AAA    1966
GAA GGC TGT GGC CAA AAG CCC CGT ATC AAA CTG CCA TTT CTT CCG GTT    2014
TCT GTG GAC CTT GTG GCC AGG TGC TCT TCC CGA GCC ACA GGT GTT CTG    2062
TGA GCT TGC TTG TGT GTG TGT GCG CGT GTG CGT GTG TTG CTC AAA TAA    2110
AGT TTG TAC GCT TTC TGA AAA AAA AAA                                2137
```

FIG.8C

Nucleotide sequence of human granulin/epithelin precursor (human GP88).
Human Granulin Genbank M75161$

```
cgcaggcaga ccatgtggac cttggtgagc tgggtggcct taacagcagg gctggtggct
ggaacgcggt gcccagatgg tcagttctgc cctgtggcct gctgcctgga ccccggagga
gccagctaca gctgctgccg tccccttctg gacaaatggc ccacaacact gagcaggcat
ctgggtggcc cctgccaggt tgatgcccac tgctctgccg gccactcctg catctttacc
gtctcaggga cttccagttg ctgcccttc ccagaggccg tggcatgcgg ggatggccat
cactgctgcc cacggggctt ccactgcagt gcagacggga gatcctgctt ccaaagatca
ggtaacaact ccgtgggtgc catccagtgc cctgatagtc agttcgaatg cccggacttc
tccacgtgct gtgttatggt cgatggctcc tgggggtgct gccccatgcc ccaggcttcc
tgctgtgaag acagggtgca ctgctgtccg cacggtgcct tctgcgacct ggttcacacc
cgctgcatca cacccacggg cacccacccc ctggcaaaga agctccctgc cagaggact
aacagggcag tggccttgtc cagctcggtc atgtgtccgg acgcacggtc ccggtgccct
gatggttcta cctgctgtga gctgcccagt gggaagtatg gctgctgccc aatgcccaac
gccacctgct gctccgatca cctgcactgc tgcccccaag acactgtgtg tgacctgatc
cagagtaagt gcctctccaa ggagaacgct accacggacc tcctcactaa gctgcctgcg
cacacagtgg gcgatgtgaa atgtgacatg gaggtgagct gcccagatgg ctatacctgc
tgccgtctac agtcgggggc ctggggctgc tgccctttta cccaggctgt gtgctgtgag
gaccacatac actgctgtcc cgcggggttt acgtgtgaca cgcagaaggg tacctgtgaa
caggggcccc accaggtgcc ctggatggag aaggccccag ctcacctcag cctgccagac
ccacaagcct tgaagagaga tgtccctgt gataatgtca gcagctgtcc ctcctccgat
acctgctgcc aactcacgtc tggggagtgg ggctgctgtc caatcccaga ggctgtctgc
tgctcggacc accagcactg ctgcccccag cgatacacgt gtgtagctga ggggcagtgt
cagcgaggaa gcgagatcgt ggctggactg gagaagatgc ctgcccgccg cggttcctta
tcccacccca gagacatcgg ctgtgaccag cacaccagct gcccggtggg cggaacctgc
tgcccgagcc agggtgggag ctgggcctgc tgccagttgc cccatgctgt gtgctgcgag
gatcgccagc actgctgccc ggctggctac acctgcaacg tgaaggctcg atcctgcgag
aaggaagtgg tctctgccca gcctgccacc ttcctggccc gtagccctca cgtgggtgtg
aaggacgtgg agtgtgggga aggacacttc tgccatgata ccagacctg ctgccgagac
aaccgacagg gctggcctg ctgtccctac gcccagggcg tctgttgtgc tgatcggcgc
cactgctgtc ctgctggctt ccgctgcgca cgcaggggta ccaagtgttt gcgcagggag
gccccgcgct gggacgcccc tttgagggac ccagccttga cacagctgct gtgagggaca
gtactgaaga ctctgcagcc ctcgggaccc cactcggagg gtgccctctg ctcaggcctc
gtactgaaga ctctgcagcc ctcgggaccc cactcggagg gtgccctctg ctcaggcctc
cctagcacct cccctaacc aaattctccc tggacccat tctgagctcc ccatcaccat
gggaggtggg gcctcaatct aaggcccttc cctgtcagaa gggggttgag gcaaaagccc
attacaagct gccatcccct ccccgtttca gtggaccctg tggccaggtg cttttccta
tccacagggg tgtttgtgtg ttgggtgtgc tttcaataaa gtttgtcact ttctt*
```

FIG.9A

Amino-acid sequence of human granulin/epithelin precursor (human GP88).

MWTLVSWVALTAGLVAGTRCPDGQFCPVACCLDPGGASYSCCRP
LLDKWPTTLSRHLGGPCQVDAHCSAGHSCIFTVSGTSSCCPFPEAVACGDGHHCCPRG
FHCSADGRSCFQRSGNNSVGAIQCPDSQFECPDFSTCCVMVDGSWGCCPMPQASCCED
RVHCCPHGAFCDLVHTRCITPTGTHPLAKKLPAQRTNRAVALSSSVMCPDARSRCPDG
STCCELPSGKYGCCPMPNATCCSDHLHCCPQDTVCDLIQSKCLSKENATTDLLTYLPA
HTVGDVKCDMEVSCPDGYTCCRLQSGAWGCCPFTQAVCCEDHIHCCPAGFTCDTQKGT
CEQGPHQVPWM<u>EKAPAHLSLPDPQALKRD</u>VPCDNVSSCPSSDTCCQLTSGEWGCCPIP
EAVCCSDHQHCCPQRYTCVAEGQCQRGSEIVAGLEKMPARRGSLSHPRDIGCDQHTSC
PVGGTCCPSQGGSWACCQLPHAVCCEDRQHCCPAGYTCNVKARSCEKEVVSAQPATFL
ARSPHVGVKDVECGEGHFCHDNQTCCRDNRQGWACCPYAQGVCCADRRHCCPAGFRC<u>A
RRGTKCLRREAPR</u>WDAPLRDPALRQLL*

FIG.9B

Mouse GP88 protein sequence

MWVLMSWLAFAAGLVAG 17

TQCPDGQF-CPVA--CCLDQG-GANYSCCNPLLDTWPRITSHHL 57

DGSC-QTHGHCPAGY-SCLLTVSGTS-SCCPFSKGVSCGDGYHCCPQGFHCSADGKSCFQMSDNPL 120

GAVQCPGSQFECPDSATCCIMVD-G-SWGCCPMPQASCCEDRVHCCPHGASCDLVHTRCVSPTGTHTLLKKFPAQKTNAAVSLPFS 204 g

VVCPDAKTQCPDDSTCCELP-TGK-YGCCPMPNAICCSDHLHCCPQDTVCDLIQSKCLSKNYTTDLLTKLPGYPVK 278 f

EVKC-DMEVSCPEGYTCCALN-TGA-WGCCPFAKAVCCEEDHIHCCPAGFOCHTEKGICEMGILQVPWMKKVIAPRRLPDPQILKS 360 2,B

DIPCDDFIR-CPTNNTCCKLN-SGD-WGCCPIPEAVCCSDNQHCCPQGFTCLAQGY-CQKGDTMVAGLEKIPARQTTPLQIG 438 1,A

DIGCDUHT-SCPVGQTCCPSLK-G-SWACCQLPHAVCCEDRQHCCPAGYTCNVKARTCEKDVDFIQPPVLLTLGPKVG 513 C

NVECGEGHF-CHDNQTCCKDSA-GV-WACCPYLKGVCCRDGRHCCPGGFHCSARGTKCLAKKIPRWDMFLADPVPRPLL 589 D e consensus sequence:

C......C......CC......G.....CC.......CC..D..HCCP....C........C 1,2:mouse epithelin 1,2.
A,B,C,D,e,f,g: granulin A,B,C,D,E,F,G;N-terminus of granulin A,B,C,D have been sequenced.
Mouse epithelin precursor sequence is from Plowman et al.(1992).

FIG.10

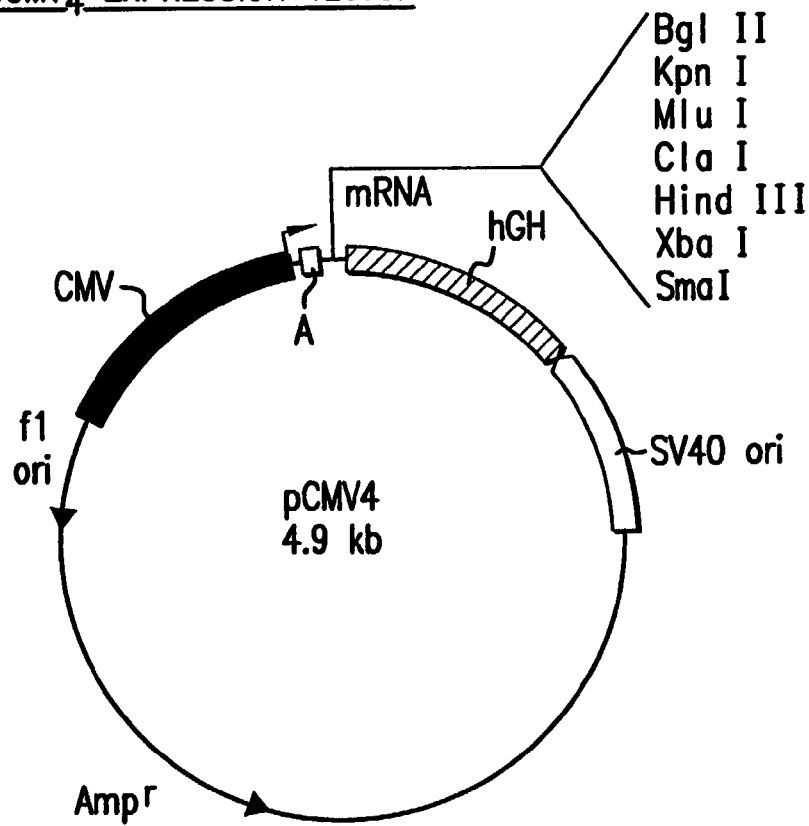
FIG. 11

GP88 EXPRESSION IN NON TUMORIGENIC (MCF 10A)
AND MALIGNANT (MCF 7, MDA-468) HUMAN
MAMMARY EPITHELIAL CELLS

GP88 EXPRESSION IS INHIBITED BY ANTISENSE GP88
cDNA TRANSFECTION IN HUMAN BREAST
CARCINOMA MDA-468

METHODS AND KITS FOR DIAGNOSING TUMORIGENICITY

This application is a continuation-in-part of U.S. application Ser. No. 09/456,886, filed Dec. 8, 1999 now U.S. Pat. No. 6,720,159, which is a divisional of U.S. application Ser. No. 08/991,862, filed Dec. 16, 1997, now U.S. Pat. No. 6,309,826, which is a continuation-in-part of U.S. patent application Ser. No. 08/863,079, filed May 23, 1997, now abandoned.

BACKGROUND OF THE INVENTION

This invention relates to cell biology, physiology and medicine, and concerns an 88 kDa glycoprotein growth factor ("GP88") and compositions and methods which affect the expression and biological activity of GP88. This invention also relates to kit products, compositions and methods which are useful for diagnosis and treatment of diseases including cancer.

REFERENCES

Several publications are referenced herein by Arabic numerals within parenthesis. Full citations for these references may be found at the end of the specification immediately preceding the claims.

BACKGROUND OF THE INVENTION

The proliferation and differentiation of cells in multicellular organisms is subject to a highly regulated process. A distinguishing feature of cancer cells is the absence of control over this process; proliferation and differentiation become deregulated resulting in uncontrolled growth. Significant research efforts have been directed toward better understanding this difference between normal and tumor cells. One area of research focus is growth factors and, more specifically, autocrine growth stimulation.

Growth factors are polypeptides which carry messages to cells concerning growth, differentiation, migration and gene expression. Typically, growth factors are produced in one cell and act on another cell to stimulate proliferation. However, certain malignant cells, in culture, demonstrate a greater or absolute reliance on an autocrine growth mechanism. Malignant cells which observe this autocrine behavior circumvent the regulation of growth factor production by other cells and are therefore unregulated in their growth.

Study of autocrine growth control advances understanding of cell growth mechanisms and leads to important advances in the diagnosis and treatment of cancer. Toward this end, a number of growth factors have been studied, including insulin-like growth factors ("IGF1" and "IGF2"), gastrin-releasing peptide ("GRP"), transforming growth factors alpha and beta ("TGF-a" and "TGF-b"), and epidermal growth factor ("EGF").

The present invention is directed to a recently discovered growth factor. This growth factor was first discovered in the culture medium of highly tumorigenic "PC cells," an insulin-independent variant isolated from the teratoma derived adipogenic cell line 1246. This growth factor is referred to herein as "GP88." GP88 has been purified and structurally characterized. Amino acid sequencing of GP88 indicates that GP88 has amino acid sequence similarities with the mouse granulin/epithelin precursor.

Granulins/epithelins ("grn/epi") are 6 kDa polypeptides and belong to a novel family of double cysteine rich polypeptides. U.S. Pat. No. 5,416,192 (Shoyab et al.) is directed to 6 kDa epithelins, particularly epithelin 1 and epithelin 2. According to Shoyab, both epithelins are encoded by a common 63.5 kDa precursor, which is processed into smaller forms as soon as it is synthesized, so that the only natural products found in biological samples are the 6 kDa forms. Shoyab et al. teaches that the epithelin precursor is biologically inactive.

Contrary to the teachings of Shoyab et al., the inventor's laboratory has demonstrated that the precursor is not always processed as soon as it is synthesized. Studies, conducted in part by this inventor, have demonstrated that the precursor (i.e., GP88) is in fact secreted as an 88 kDa glycoprotein with an N-linked carbohydrate moiety of 20 kDa. Analysis of the N-terminal sequence of GP88 indicates that GP88 starts at amino acid 17 of the grn/epi precursor, demonstrating that the first 17 amino acids from the protein sequence deduced from the precursor cDNA correspond to a signal peptide compatible with targeting for membrane localization or for secretion. Also in contrast to the teachings of Shoyab et al., GP88 is biologically active and has growth promoting activity, particularly as an autocrine growth factor for the producer cells.

Diagnosis of cancer often requires sampling a biopsy of a tissue suspected of being tumorigenic, testing the tissue sample to determine if a tumor marker is present, and determining if the tissue sample is tumorigenic. Biopsy procedures can be risky and painful depending on the location of the tissue and the condition of the patient. In addition, the trauma inflicted by biopsy procedures may increase the risk of malignancy. A study reported in the British Medical Journal identified biopsy as the strongest risk factor for testicular cancer. Swerdlow et al., BMJ 1997;314:1507. Biopsy has also been identified as a risk factor in breast, liver, and other cancers. In addition, a study conducted at the Johns Hopkins University concluded that misdiagnosis following biopsies occurs at a significant rate. Kronz et al., Cancer: Dec. 1, 1999, vol. 86, no. 11 pp 2426–2435. Misdiagnosis may be due, in part, to the small sample sizes obtained from needle biopsies and other procedures that capture only small tissue samples. Small biopsy sample sizes reduce patient risk. Id. However, the risk of misdiagnosis increases when only a small tissue sample is utilized. Id.

What is needed are new methods and kits for diagnosis, treatment, and prevention of cancer, and particularly methods and kits that avoid risks associated with biopsy of tissue.

BRIEF SUMMARY OF THE INVENTION

The inventor has now unexpectedly discovered that a glycoprotein (GP88), which is expressed in a tightly regulated fashion in normal cells, is overexpressed and unregulated in highly tumorigenic cells derived from the normal cells, that GP88 acts as a stringently required growth stimulator for the tumorigenic cells and that inhibition of GP88 expression or action in the tumorigenic cells results in an inhibition of the tumorigenic properties of the overproducing cells.

The inventor has further discovered methods of detecting GP88 in biological fluids at concentrations as low as about 0.1 nanograms of GP88 per milliliter (ng/ml). An embodiment of the invention provides non-invasive methods and kits for detecting GP88 in a biological fluid (e.g., whole blood, plasma, serum, lymph, saliva, and urine).

Another embodiment of the invention provides methods and kits for diagnosing tumorigenicity by measuring the level of GP88 in a biological fluid and determining whether the measured level of GP88 is sufficient to indicate tumorigenicity. In yet further embodiments, the invention provides methods and kits for diagnosing tumorigenicity by measuring the level of GP88 protein in a first biological fluid sample from a patient, measuring the level of GP88 in a second or subsequent biological fluid sample taken from the same patient, and diagnosing tumorigenicity by determining whether the level of GP88 in the second biological fluid sample is higher than the level in the first biological fluid by an amount sufficient to indicate tumorigenicity.

Further embodiments of the invention provide methods and kits for determining whether a patient is responding to anti-tumorigenic therapy by measuring the level of GP88 in serum. If the serum concentration of GP88 in a patient receiving anti-tumorigenic therapy is greater than a benchmark ascribed to the particular patient (for example, at least about 100 ng/ml), then the patient is not responding to anti-tumorigenic therapy. In another embodiment of the invention, a method for treating or preventing the re-occurrence of cancer is provided. In accordance with this embodiment, the concentration of GP88 in a biological fluid sample taken from a patient is determined. A GP88 antagonist is administered to the patient in an amount sufficient to treat or prevent reoccurrence of cancer if the concentration of GP88 in the biological fluid is greater than a benchmark ascribed to the particular patient (for example, at least about 50 ng/ml).

This invention also provides GP88 antagonizing compositions capable of inhibiting the expression or activity of GP88, methods for treating diseases associated with a defect in GP88 quantity or activity such as but not limited to cancer in a mammal in tissues including, for example, blood, cerebrospinal fluid, serum, plasma, urine, nipple aspirate, liver, kidney, breast, bone, bone marrow, testes, brain, ovary, skin, and lung, methods for determining the susceptibility of a subject to diseases associated with a defect in GP88 expression or action, methods for measuring susceptibility to GP88 antagonizing therapy, and methods, reagents, and kits for the in vitro and in vivo detection of GP88 and tumorigenic activity in cells.

Additional objects and advantages of the invention will be set forth in part in the description that follows, and in part will be obvious from the description, or may be learned by the practice of the invention.

To achieve the objects and in accordance with the purpose of the invention, as embodied and properly described herein, the present invention provides compositions for diagnosis and treatment of diseases, such as breast cancer, in which cells exhibit an altered expression of GP88 or altered response to GP88.

Use of the term "altered expression" herein means increased expression or overexpression of GP88 by a factor of at least two-fold, and at times by a factor of 10 or more, based on the level of mRNA or protein as compared to corresponding normal cells or surrounding peripheral cells. The term "altered expression" also means expression which became unregulated or constitutive without being necessarily elevated. Use of the terms increased or altered "response" to GP88 means a condition wherein increase in any of the biological functions (e.g., growth, differentiation, viral infectivity) conferred by GP88 results in the same or equivalent condition as altered expression of GP88.

Use of the term "GP88" herein means epithelin/granulin precursor in cell extracts and extracellular fluids, and is intended to include not only GP88 according to the amino acid sequences included in FIGS. 8 or 9, which are of mouse and human origins, but also GP88 of other species. In addition, the term also includes functional derivatives thereof having additional components such as a carbohydrate moiety including a glycoprotein or other modified structures.

Also intended by the term GP88 is any polypeptide fragment having at least 10 amino-acids present in the above mentioned sequences. Sequences of this length are useful as antigens and for making immunogenic conjugates with carriers for the production of antibodies specific for various epitopes of the entire protein. Such polypeptides are useful in screening such antibodies and in the methods directed to detection of GP88 in biological fluids. It is well known in the art that peptides are useful in generation of antibodies to larger proteins (7). In one embodiment of this invention, it is shown that peptides from 12–19 amino-acids in length have been successfully used to develop antibodies that recognize the full length GP88.

The polypeptide of this invention may exist covalently or non-covalently bound to another molecule. For example, it may be fused to one or more other polypeptides via one or more peptide bonds such as glutathione transferase, polyhistidine, or myc tag.

The polypeptide is sufficiently large to comprise an antigenetically distinct determinant or epitope which can be used as an immunogen to reproduce or test antibodies against GP88 or a functional derivative thereof.

One embodiment includes the polypeptide substantially free of other mammalian peptides. GP88 of the present invention can be biochemically or immunochemically purified from cells, tissues or a biological fluid. Alternatively, the polypeptide can be produced by recombinant means in a prokaryotic or eukaryotic expression system and host cells.

"Substantially free of other mammalian polypeptides" reflects the fact that the polypeptide can be synthesized in a prokaryotic or a non-mammalian or mammalian eukaryotic organism, if desired. Alternatively, methods are well known for the synthesis of polypeptides of desired sequences by chemical synthesis on solid phase supports and their subsequent separation from the support. Alternatively, the protein can be purified from tissues or fluids of mammals where it naturally occurs so that it is at least 90% pure (on a weight basis) or even 99% pure, if desired, of other mammalian polypeptides, and is therefore substantially free from them. This can be achieved by subjecting the tissue extracts or fluids to standard protein purification such as on immunoabsorbants bearing antibodies reactive against the protein. One embodiment of the present invention describes purification methods for the purification of naturally occurring GP88 and of recombinant GP88 expressed in baculovirus infected insect cells. Alternatively, purification from such tissues or fluids can be achieved by a combination of standard methods such as but not limited to the ones described in reference (4).

As an alternative to a native purified or recombinant glycoprotein or polypeptide, "GP88" is intended to also include functional derivatives. By functional derivative is meant a "fragment," "variant," "analog," or "chemical derivative" of the protein or glycoprotein as defined below. A functional derivative retains at least a portion of the function of the full length GP88 which permits its utility in accordance with the present invention.

A "fragment" of GP88 refers to any subset of the molecule that is a shorter peptide retaining the tumorigenic properties of GP88. This corresponds for example but is not limited to regions such as K19T and S14R for mouse GP88, and E19V and A14R (equivalent to murine K19T and S14R, respectively) for human GP88.

A "variant" of GP88 refers to a molecule substantially similar to either the entire peptide or a fragment thereof. Variant peptides may be prepared by direct chemical synthesis of the variant peptide using methods known in the art.

Alternatively, amino acid sequence variants of the peptide can be prepared by modifying the DNA which encodes the synthesized protein or peptide. Such variants include, for example, deletions, insertions, or substitutions of residues within the amino-acid sequence of GP88. Any combination of deletion, insertion, and substitution may also be made to arrive at the final construct, provided the final construct possesses the desired activity. The mutation that will be made in the DNA encoding the variant peptide must not alter the reading frame and preferably will not create complementary regions that could produce secondary mRNA structures. At the genetic level these variants are prepared by site directed mutagenesis (8) of nucleotides in the DNA encoding the peptide molecule thereby producing DNA encoding the variant, and thereafter expressing the DNA in recombinant cell culture. The variant typically exhibits the same qualitative biological activity as the nonvariant peptide.

An "analog" of GP88 protein refers to a non-natural molecule substantially similar to either the entire molecule or a fragment thereof.

A "chemical derivative" contains additional chemical moieties not normally a part of the peptide or protein. Covalent modifications of the peptide are also included within the scope of this invention. Such modifications may be introduced into the molecule by reacting targeted amino-acid residues of the peptide with an organic derivatizing agent that is capable of reacting with selected side chains or terminal amino-acid residues. Most commonly derivatized residues are cysteinyl, histidyl, lysinyl, arginyl, tyrosyl, glutaminyl, asparaginyl and amino terminal residues. Hydroxylation of proline and lysine, phosphorylation of hydroxyl groups of seryl and threonyl residues, methylation of the alpha-amino groups of lysine, histidine, and histidine side chains, acetylation of the N-terminal amine and amidation of the C-terminal carboxylic groups. Such derivatized moieties may improve the solubility, absorption, biological half life and the like. The moieties may also eliminate or attenuate any undesirable side effect of the protein and the like. In addition, derivatization with bifunctional agents is useful for cross-linking the peptide to water insoluble support matrices or to other macromolecular carriers. Commonly used cross-linking agents include glutaraldehyde, N-hydroxysuccinimide esters, homobifunctional imidoesters, 1,1-bis(-diazoloacetyl)-2-phenylethane, and bifunctional maleimides. Derivatizing agents such as methyl-3-[9-azidophenyl)]dithiopropioimidate yield photoactivatable intermediates that are capable of forming crosslinks in the presence of light. Alternatively, reactive water-insoluble matrices such as cyanogen bromide activated carbohydrates and the reactive substrates described in U.S. Pat. Nos. 3,969,287 and 3,691,016 may be employed for protein immobilization.

Use of the term GP88 "antagonizing agents" herein means any composition that inhibits or blocks GP88 expression, production or secretion, or any composition that inhibits or blocks the biological activity of GP88. This can be achieved by any mode of action such as but not limited to the following:

(A) GP88 antagonizing agents include any reagent or molecule inhibiting GP88 expression or production including but not limited to:

(1) antisense GP88 DNA or RNA molecules that inhibit GP88 expression by inhibiting GP88 translation;

(2) reagents (hormones, growth factors, small molecules) that inhibit GP88 mRNA and/or protein expression at the transcriptional, translational or post-translational levels;

(3) factors, reagents or hormones that inhibit GP88 secretion;

(B) GP88 antagonizing agents also include any reagent or molecule that will inhibit GP88 action or biological activity such as but not limited to:

(1) neutralizing antibodies to GP88 that bind the protein and prevent it from exerting its biological activity;

(2) antibodies to the GP88 receptor that prevent GP88 from binding to its receptor and from exerting its biological activity;

(3) competitive inhibitors of GP88 binding to its receptors;

(4) inhibitors of GP88 signaling pathways.

Specific examples presented herein provide a description of preferred embodiments, particularly the use of neutralizing antibodies to inhibit GP88 biological action and the growth of caner cells, including but not limited to breast cancer cells; the use of antisense GP88 cDNA and antisense GP88 oligonucleotides to inhibit GP88 expression leading to inhibition of the tumorigenic properties of PC cells; characterization of GP88 receptors on cell surfaces of several cell lines including the mammary epithelial cell line C57MG, the 1246 and PC cell lines and the mink lung epithelial cell line CCL64.

In one embodiment of the invention, the GP88 antagonizing agents are antisense oligonucleotides to GP88. The antisense oligonucleotides preferably inhibit GP88 expression by inhibiting translation of the GP88 protein.

Alternatively, such a composition may comprise reagents, factors or hormones that inhibit GP88 expression by regulating GP88 gene transcriptional activity. Such a composition may comprise reagents, factors or hormones that inhibit GP88 post-translational modification and its secretion. Such a composition may comprise reagents that act as GP88 antagonists that block GP88 activity by competing with GP88 for binding to GP88 cell surface receptors. Alternatively, such a composition may comprise factors or reagents that inhibit the signaling pathway transduced by GP88 once binding to its receptors on diseased cells.

Alternatively, the composition may comprise reagents that block GP88 action such as an antibody specific to GP88 that neutralizes its biological activity, or an antibody to the GP88 receptor that blocks its activity.

The antibodies of the invention (neutralizing and others) are preferably used as a treatment for breast cancer, other cancers, or other diseases in cells which exhibit an increased expression of GP88. By the term "neutralizing" it shall be understood that the antibody has the ability to inhibit or block the normal biological activity of GP88, including GP88's ability to stimulate cell proliferation or to induce tumor growth in experimental animals and in humans. An effective amount of anti-GP88 antibody is administered to an animal, including humans, by various routes. In an alternative embodiment, the anti-GP88 antibody is used as a diagnostic to detect cells which exhibit an altered (increased) expression of GP88 as occurring in diseases such as but not limited to cancers (e.g., breast cancer), and to identify diseased cells whose growth is dependent on GP88 and which will respond to GP88 antagonizing therapy. In yet another embodiment, the anti-GP88 antibody is used to deliver compounds such as cytotoxic factors or antisense oligonucleotides to cells expressing or responsive to GP88. The cytotoxic factors may be attached, linked, or associated with the anti-GP88 antibody.

The antisense oligonucleotides of the invention are also used as a treatment for cancer in cells which exhibit an increased expression of GP88. An effective amount of the antisense oligonucleotide is administered to an animal, including humans, by various routes.

The present invention also provides a method for determining the susceptibility to diseases associated with a defect in GP88 expression or action which comprises obtaining a sample of biological fluid or tissue and measuring the amount of GP88 in the fluid or tissue or measuring the susceptibility of the cells to respond to GP88. In the case of cancer (e.g., breast cancer), the amount of GP88 being proportional to the susceptibility to the cancer.

The present invention also provides a method for measuring the degree of severity of cancer (e.g., breast cancer) which comprises obtaining a sample of biological fluid or tissue and measuring the amount of GP88 in the fluid or tissue sample, the amount of GP88 being proportional to the degree or severity of the cancer. In one embodiment of the invention, the tissue sample is derived from serum, lymph, or urine.

The present invention also provides a method for measuring susceptibility to GP88 antagonizing therapy which comprises obtaining a sample of the diseased tissue (biopsy) or a tissue suspected of being diseased, maintaining the cells derived from the sample in culture, treating the cells derived from the culture with anti-GP88 neutralizing antibody and determining if the neutralizing antibody inhibits the cell growth. The ability of the antibody to inhibit cell growth is indicative that the cells are dependent on GP88 to proliferate and is predictive that GP88 antagonizing therapy will be efficacious.

The present invention also provides a method for determining the susceptibility to cancer associated with an abnormality in GP88 receptor level or activity which comprises obtaining a sample of tissue and measuring the amount of GP88 receptor protein or mRNA in the tissue or measuring the tyrosine kinase activity of the receptor in the tissue (GP88 binding to its receptor induces tyrosine phosphorylation of cellular proteins including the receptor for GP88).

The present invention also provides a method for targeting GP88 antagonizing reagents to the diseased site by conjugating them to an anti-GP88 antibody or an anti-GP88 receptor antibody.

The accompanying drawings, which are incorporated in and constitute a part of this specification, illustrate embodiments of the invention and, together with the description, serve to explain the principles of the invention.

BRIEF DESCRIPTION OF THE DRAWINGS

FIG. 3 shows C3H mice injected subcutaneously with $10^6$ antisense GP88 transfected PC cells (bottom) and with empty vector transfected control PC cells (top).

FIGS. 8A–8C show the nucleotide and deduced amino-acid sequence of mouse GP88. Peptide regions used as antigens to raise anti-GP88 antibodies K19T and S14R are underlined. The region cloned in the antisense orientation in the pCMV4 mammalian expression vector is indicated between brackets.

FIG. 9A shows the nucleotide sequence of human GP88 cDNA. Indicated between brackets is the region cloned in the antisense orientation into the pcDNA3 mammalian expression system; and FIG. 9B shows the deduced amino-acid sequence of human GP88. The E19V region used as antigen to develop anti-human GP88 neutralizing antibody is underlined. It also indicates the region A14R equivalent to the mouse S14R region.

FIG. 10 shows the amino-acid sequence of mouse GP88 arranged to show the 7 and one-half repeats defined as granulins g, f, B, A, C, D and e (right side). This representation shows that the region K19T and S14R used to raise GP88 antibodies for developing anti-GP88 neutralizing antibodies is found between two epithelin/granulin repeats in what is considered a variant region. Indicated on the right hand side is the granulin classification of the repeats according to Bateman et al (6). Granulin B and granulin A are also defined as epithelin 2 and epithelin 1 respectively according to Plowman et al., 1992 (5).

FIG. 11 shows a-schematic representation of pCMV4 and a GP88 cDNA clone indicating the restriction sites used to clone GP88 antisense cDNA into the expression vector.

DETAILED DESCRIPTION OF THE INVENTION

Reference will now be made in detail to the presently preferred embodiments of the invention, which, together with the following examples, serve to explain the principles of the invention.

Biological Activity of GP88

The invention relates to GP88 and antitumor and antiviral compositions useful for treating and diagnosing diseases linked to altered (increased) expression of GP88. Alternatively this invention is used for treating and diagnosing diseases linked to increased responsiveness to GP88. Using a murine model system consisting of three cell lines, the inventor has shown that cells which overexpress GP88 form tumors. The parent cell line, 1246, is a C3H mouse adipogenic cell line which proliferates and differentiates into adipocytes in a defined medium under stringent regulation by insulin. The 1246 cells cannot form tumors in a syngeneic animal (C3H mouse) even when injected at a high cell density. An insulin independent cell line, 1246-3A, was isolated from 1246 cells maintained in insulin-free medium. The 1246-3A cells lost the ability to differentiate and form tumors when $10^6$ are injected subcutaneously in syngeneic mice. A highly tumorigenic cell line, PC, was developed from 1246-3A cells by an in vitro-in vivo shuttle technique. The PC cells formed tumors when $10^4$ cells were injected into syngeneic mice.

Figure 1A:
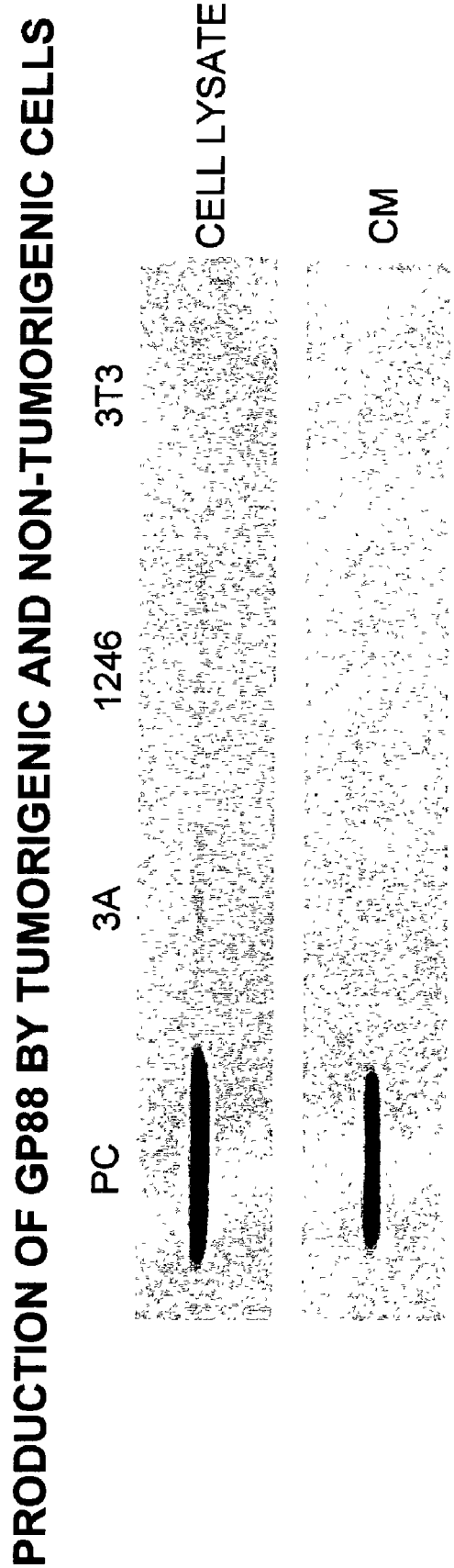
FIG. 1A compares the level of expression of GP88 protein in the 1246, 1246-3A and PC cell lines. Cells were cultured in DME-F12 medium supplemented with 2% fetal bovine serum (FBS). GP88 expression levels were measured by immunoprecipitation and Western blot analysis with anti-K19T antibody.
Figure 1B:
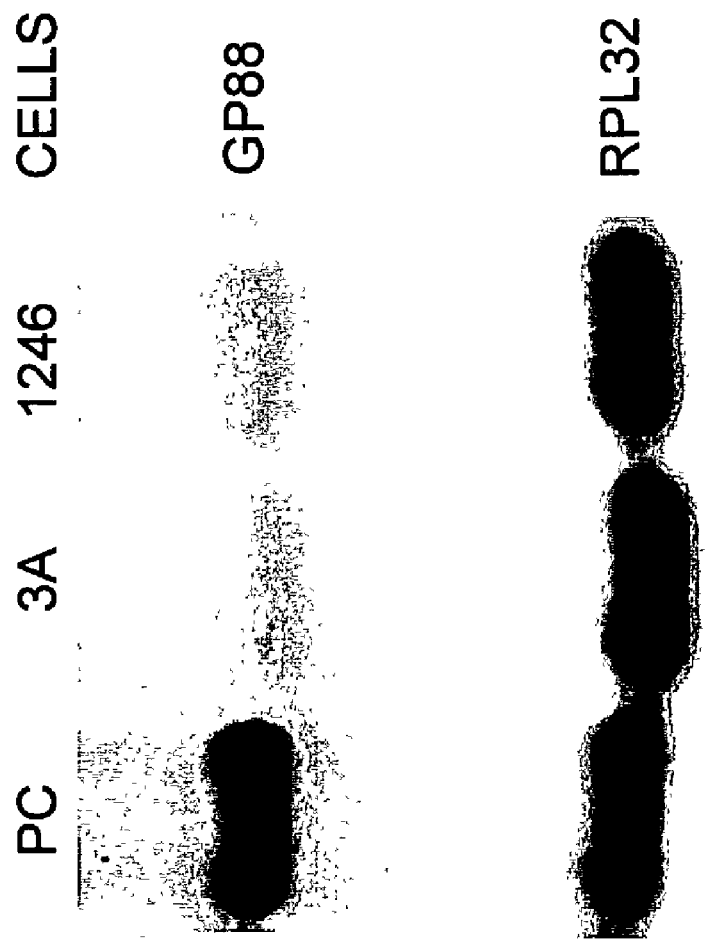
FIG. 1B compares the level of GP88 mRNA expression in the 1246, 1246-3A and PC cell lines. mRNA for RPL32 is used as an internal control for equal amounts of RNA loading.
Figure 1C:
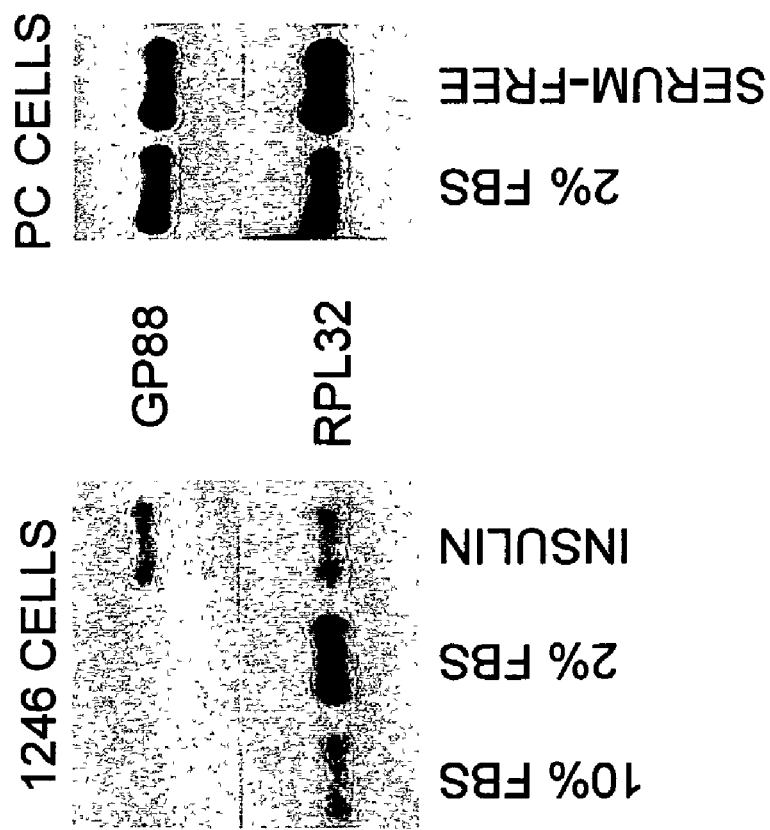
FIG. 1C compares the expression of GP88 mRNA in 1246 cells (left panel) and in PC cells (right panel) in serum-free and serum containing medium. The results show that GP88 expression in 1246 cells is inhibited by the addition of fetal bovine serum whereas such inhibition is not observed in the highly tumorigenic PC cells.

GP88 is overexpressed in the insulin-independent tumorigenic cell lines relative to the parent non-tumorigenic insulin-dependent cell line. Moreover, the degree of overexpression of GP88 positively correlates with the degree of tumorigenicity of these cells, demonstrating for the first time that GP88 is important in tumorigenesis (FIG. 1). With reference to FIG. 1, since GP88 is synthesized by cells but also secreted in culture medium, the level of GP88 was determined in cell lysates and in culture medium (CM). All cells were cultivated in DME/F12 nutrient medium supplemented with 2% fetal bovine serum. When cells reached confluency, culture medium (CM) was collected and cell lysates were prepared by incubation in buffer containing detergent followed by a 10,000×g centrifugation. Cell lysate and conditioned medium were normalized by cell number. Samples from cell lysate and conditioned medium were analyzed by Western blot analysis using an anti-GP88 antibody, as explained below.

Figure 2:
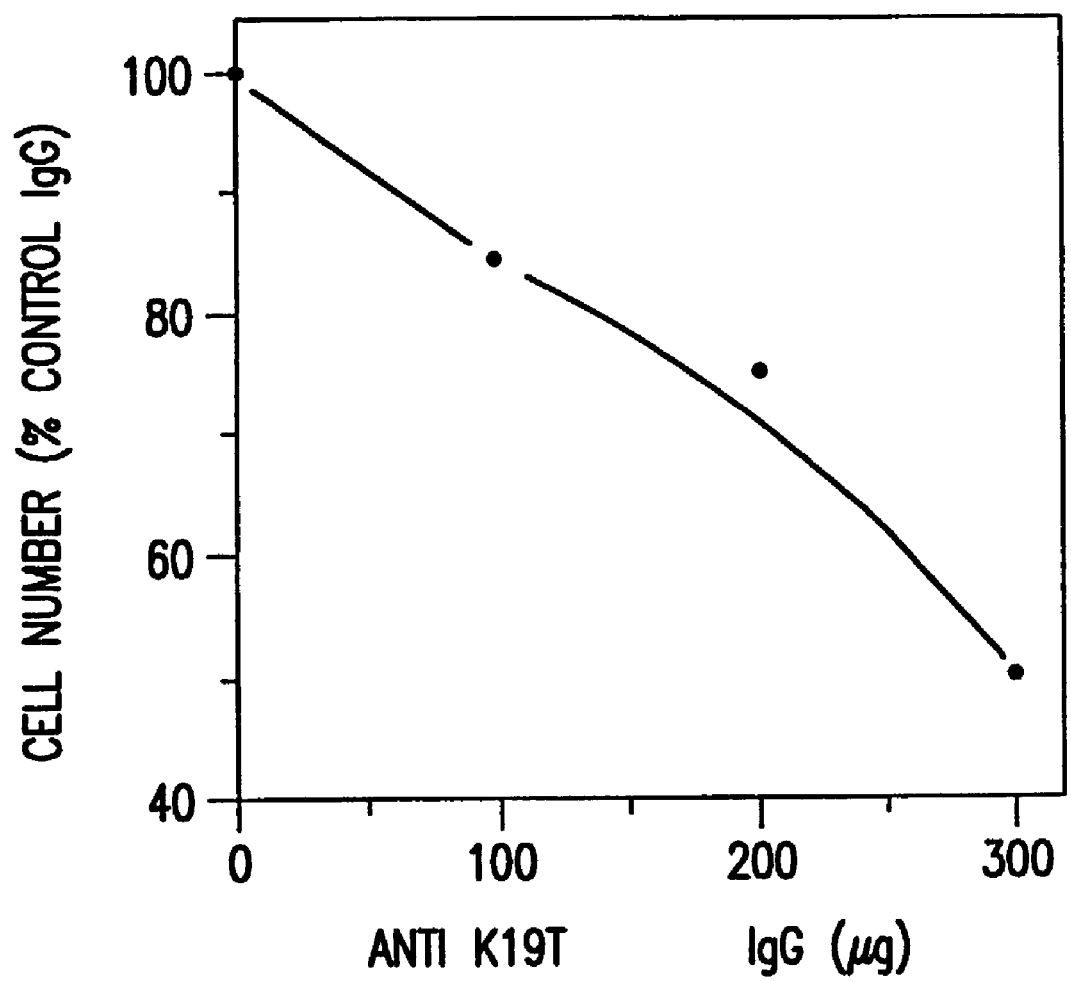
FIG. 2 illustrates the effect of treatment of the highly tumorigenic PC cells with increasing concentrations of anti-GP88 neutralizing antibody.

The development of a neutralizing antibody confirmed GP88's key role in tumorigenesis. When an anti-GP88 antibody directed to the K19T region of mouse GP88 was added to the culture medium, the growth of highly tumorigenic PC cells was inhibited in a dose dependent fashion (FIG. 2). With reference to FIG. 2, PC cells were cultivated in 96 well plates at a density $2\times10^4$ cells/well in DME/F12 medium supplemented with human fibronectin (2 µg/ml) and human transferrin (10 µg/ml). Increasing concentrations of anti-GP88 IgG fraction were added to the wells after the cells were attached. Control cells were treated with equivalent concentrations of non-immune IgG. Two days later, 0.25 mCi of $^3$H-thymidine was added per well for 6 hrs. Cells were then harvested to count $^3$H-thymidine incorporated into DNA as a measure for cell proliferation.

Moreover, when the expression of GP88 was specifically inhibited by antisense GP88 cDNA in PC cells, the production of GP88 was reduced and these PC cells could no longer form tumors in syngeneic C3H mouse. In addition, these PC cells regained responsiveness to insulin. With reference to FIG. 3 and Tables 1 and 2, C3H female mice were injected subcutaneously with $10^6$ antisense GP88 transfected PC cells (as explained below) or $10^6$ empty vector transfected PC cells. Mice were monitored daily for tumor appearance. Photographs were taken 45 days after injection of the cells. The results show that mice injected with antisense GP88 PC cells do not develop tumors, in contrast to the mice injected with empty vector transfected PC cells used as control.

TABLE 1

COMPARISON OF TUMORIGENIC PROPERTIES OF GP88 ANTISENSE TRANSFECTED CELLS, CONTROL TRANSFECTED CELLS AND PC CELLS

| CELLS INJECTED | AVERAGE DAY OF TUMOR DETECTION | NUMBER OF MICE WITH TUMORS | AVERAGE TUMOR WEIGHT (g) |
|---|---|---|---|
| PC | 15 ± 3.0 | 5/5 | 9.0 ± 3.2 |
| P14 | 15 ± 3.7 | 5/5 | 7.8 ± 2.7 |
| ASGP88 | — | 0/5 | — |

PC: Control non-transfected cells
P-14: Empty vector control transfected PC cells
ASGP88: PC cells transfected with expression vector containing GP88 antisense cDNA
Tumors were excised and weighed at 45 days. —indicates no tumor formation.

TABLE 2

COMPARISON OF PROPERTIES OF 1246, PC CELLS AND GP88 ANTISENSE CELLS

| 1246 cells | insulin independence PC cells | GP88 antisense transfection Antisense GP 88 cells |
|---|---|---|
| insulin responsive for growth and differentiation | insulin-independent for growth differentiation deficient autocrine production of insulin-related factor | recovery of insulin responsiveness for growth (differentiation?) |
| cell surface insulin receptor expression high | cell surface insulin receptor expression very low | cell surface insulin receptor expression elevated |
| GP88 expression low | GP88 expression constitutively high | GP88 expression inhibited by antisense |
| GP88 expression inhibited by serum | No inhibition by serum | |
| GP88 expression regulated by insulin | GP88 expression constitutive | recovery of insulin regulation for endogenous GP88 expression |
| non-tumorigenic | highly tumorigenic | non-tumorigenic |

Figure 4:
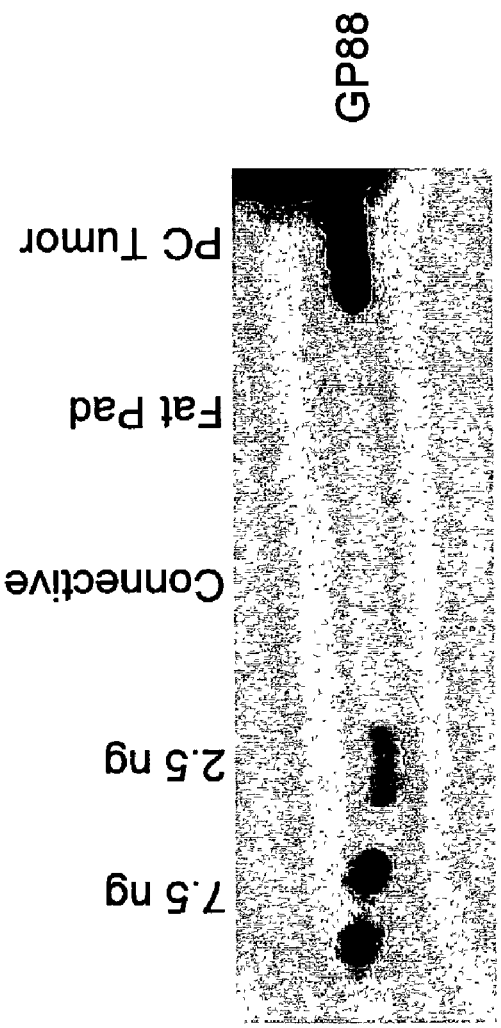
FIG. 4 shows in vivo GP88 expression levels in C3H mice tumor tissues and in surrounding normal tissues.

Comparison of the expression of GP88 indicates that in vivo GP88 levels in tumors is dramatically higher than in normal tissues (FIG. 4). C3H mice were injected with $10^6$ PC cells. Tumor bearing mice were euthanized. Tumors, fat pads and connective tissue were collected. Cell lysates were prepared by incubation in buffer containing detergent as described above for FIG. 1. Protein concentration of tissue extracts was determined, and equivalent amounts of proteins for each sample were analyzed by SDS-PAGE followed by Western blot analysis using anti-GP88 antibody to measure the content of GP88 in tissue extracts. The results showed that the level of GP88 in tumor extracts is at least 10-fold higher than in surrounding connective and fat tissues.

In normal cells (1246 cells, fibroblasts), the expression of GP88 is regulated, in particular by insulin, and inhibited by fetal bovine serum. In tumorigenic cells, a loss of regulation of normal growth leads to the increased expression of GP88 and the acquisition of GP88 dependence for growth. Therefore, inhibition of GP88 expression and/or action is an effective approach to suppression of tumorigenesis. Detection of an elevated GP88 expression in biopsies provides diagnostic analysis of tumors that are responsive to GP88 inhibition therapy.

Figure 5:
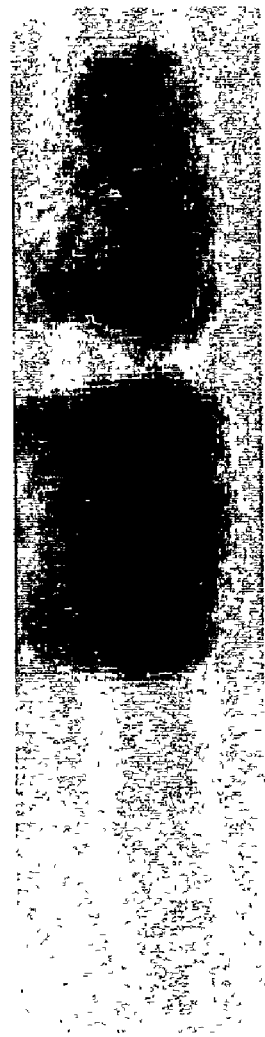
FIG. 5 shows GP88 mRNA expression levels in estrogen receptor positive and estrogen receptor negative human mammary carcinoma cell lines.
Figure 6A:
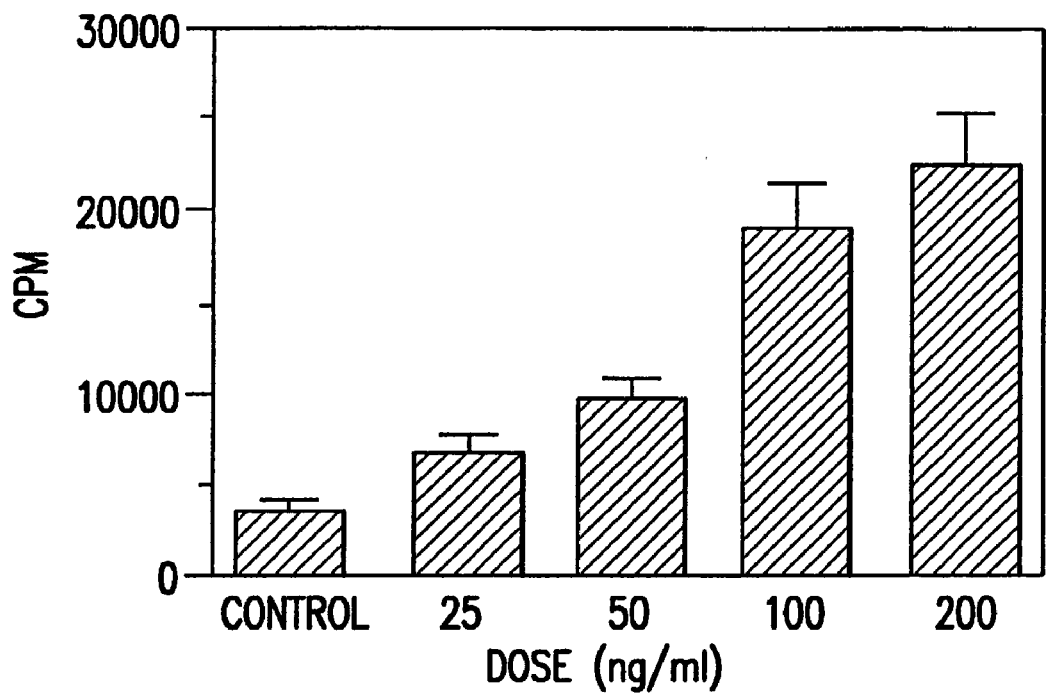
FIG. 6 shows the effect of increasing concentrations of GP88 on the growth of the mouse mammary epithelial cell line C57.
Figure 6B:
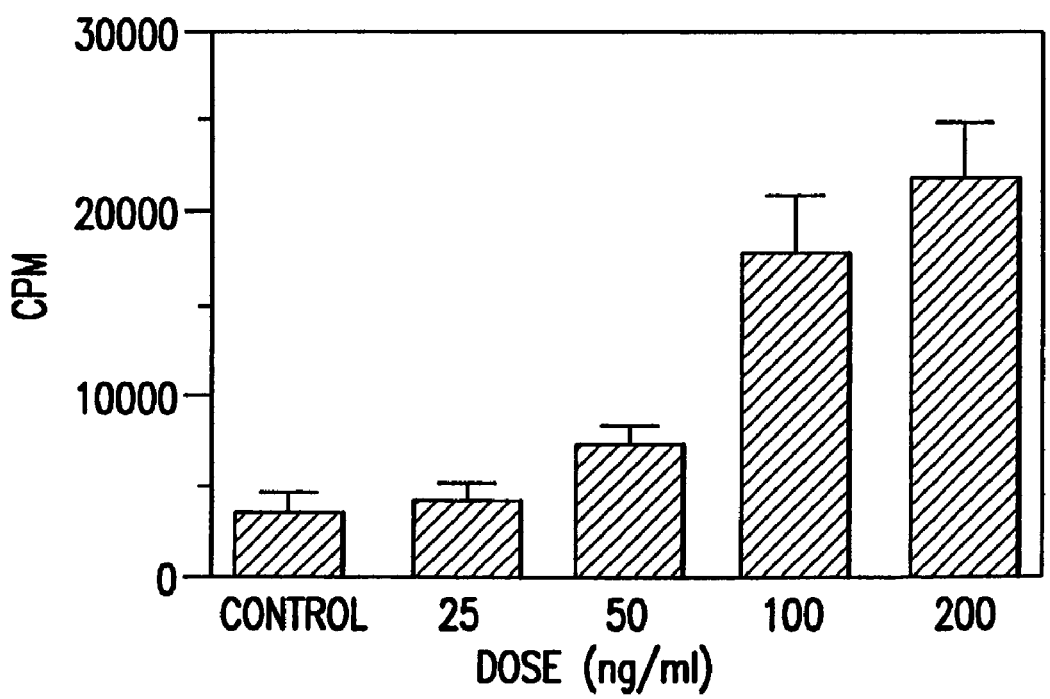
Figure 7:
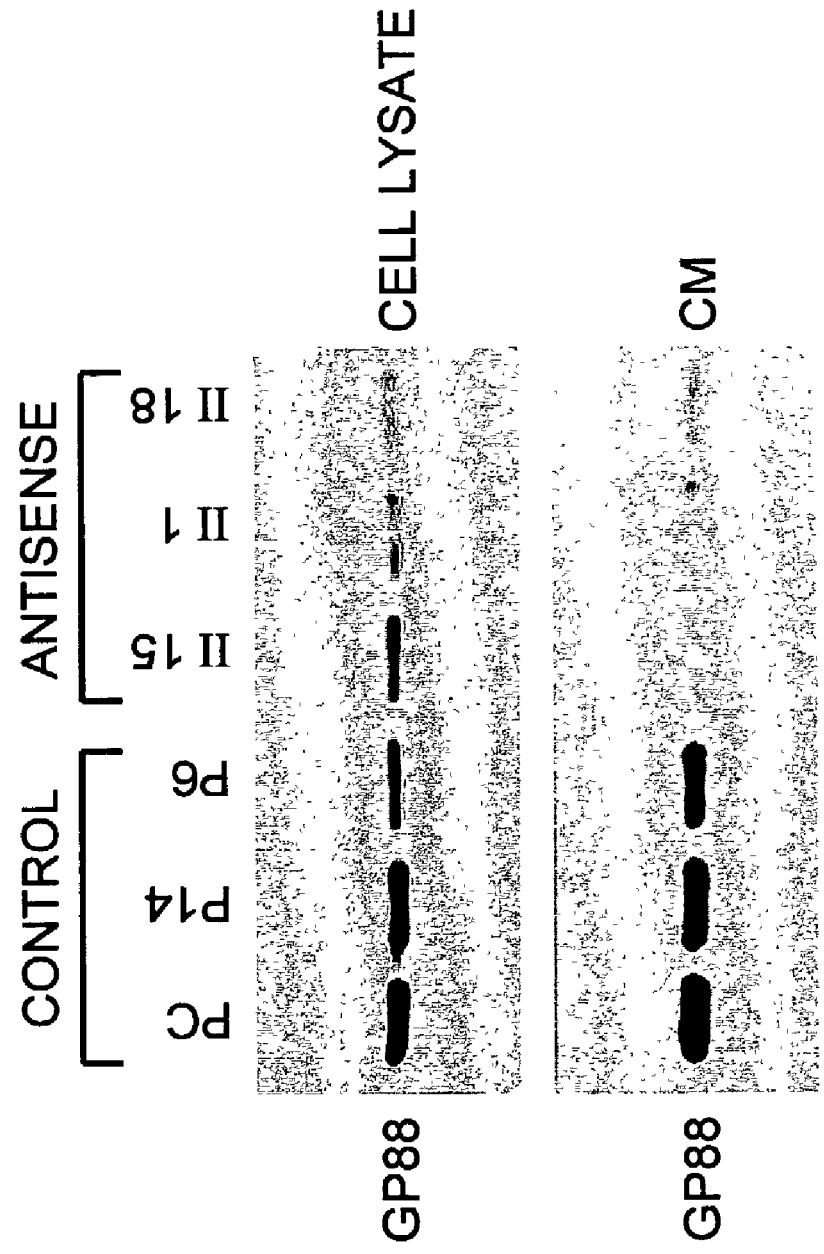
FIG. 7 shows the growth properties and tumorigenic ability of PC cells transfected with a cytomegalovirus promoter controlled expression vector containing GP88 in antisense orientation and PC cells transfected with an empty vector.
Figure 12:
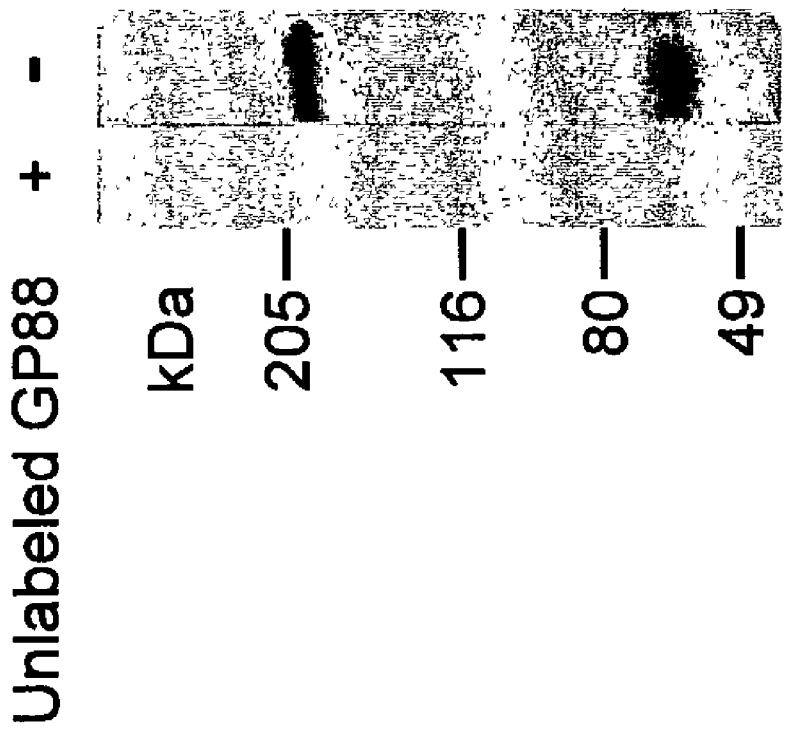
FIG. 12 shows the cross-linking of $^{125}$I-rGP88 to GP88 cell surface receptors on CCL-64 cells. The cross-linking reaction was carried out with disuccinimidyl suberate (DSS). Reaction products were analyzed by SDS-PAGE on a 7% polyacrylamide gel.
Figure 13:
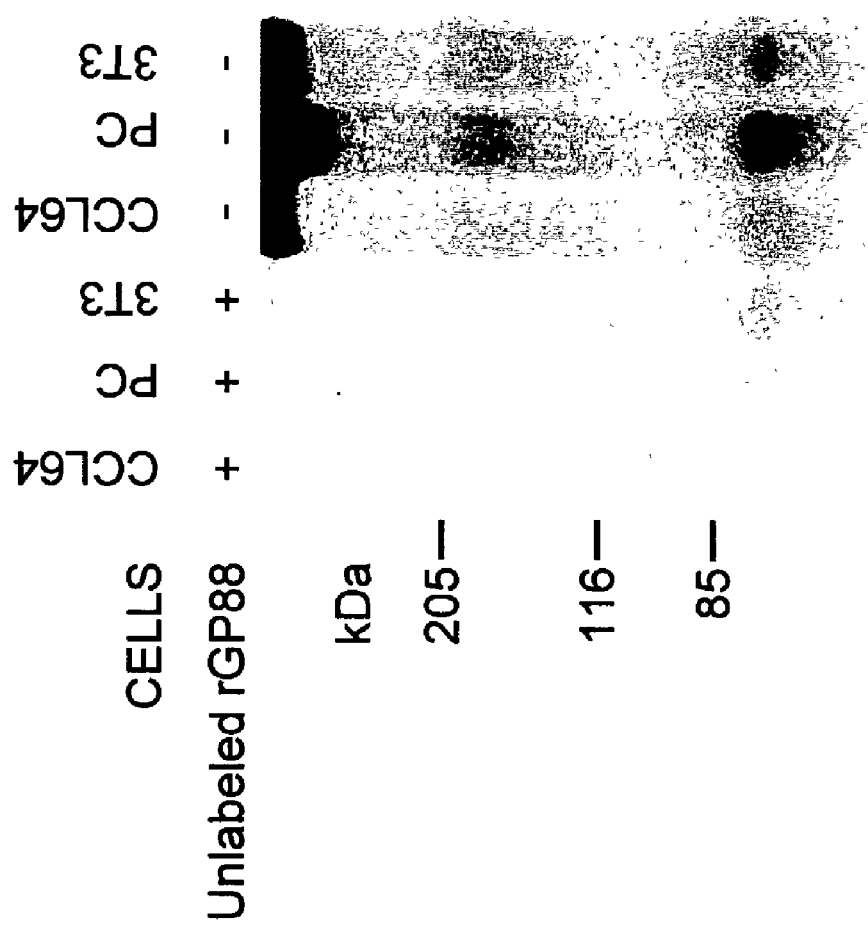
FIG. 13 shows the cross-linking of $^{125}$I-rGP88 to GP88 cell surface receptors on 3T3 fibroblasts, PC cells and C57MG mammary epithelial cells. The results show that these various cell lines display GP88 cell surface receptors of similar molecular weight as the ones on CCL64 cells (FIG. 12).
Figure 14:
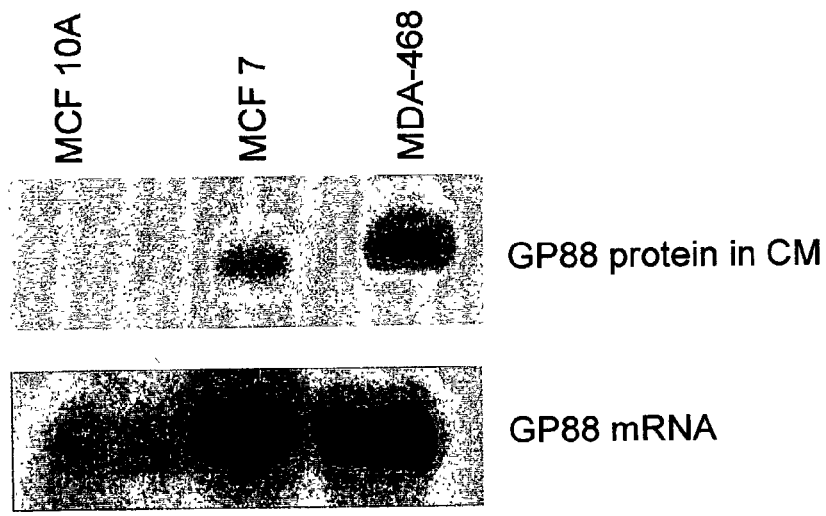
FIG. 14 shows GP88 expression levels in non-tumorigenic MCF 10A and in malignant (MCF 7, MDA-468) human mammary epithelial cells.
Figure 15:
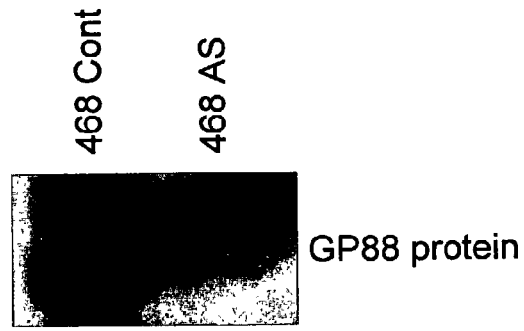
FIG. 15 shows that GP88 expression is inhibited by antisense GP88 cDNA transfection in human breast carcinoma MDA-468 cells.

GP88 is also a tumor-inducing factor in human cancers. As seen in the 1246-3A cell line, a loss of responsiveness to insulin (or to IGF-I) and a concurrent increase in malignancy has been well documented in several human cancers including but not limited to breast cancers. Specifically, breast carcinoma is accompanied by the acquisition of an insulin/IGF-I autocrine loop, which is also the starting point of the development of tumorigenic properties in the mouse model system discussed above. Furthermore, GP88 expression is elevated in human breast carcinomas. More specifically, with reference to FIG. 5, human GP88 was highly expressed in estrogen receptor positive and also in estrogen receptor negative insulin/IGF-I independent highly malignant cells. Also, GP88 is a potent growth factor for mammary epithelial cells (FIG. 6). The data in FIG. 5 was obtained by cultivating MCF7, MDA-MB-453 and MDA-MB-468 cells in DME/F12 medium supplemented with 10% fetal bovine serum (FBS). RNA was extracted from each cell line by the RNAzol method and poly-$A^+$ RNA prepared. GP88 mRNA expression was examined by Northern blot analysis with 3 μg of poly-$A^+$ RNA for each cell line using a $^{32}$P-labeled GP88 cDNA probe.

For Northern blot analysis of GP88 mRNA expression in rodent cells or tissues (mouse and rats), we used a mouse GP88 cDNA probe 311 bp in length starting at nucleotide 551 to 862 (corresponding to amino-acid sequence 160 to 270). RNA can be extracted by a variety of methods (Sambrook, Molecular Biology manual: 35) well known to people of ordinary skill in the art. The method of choice was to extract RNA using RNAzol (Cinnabiotech) or Trizol (Gibco-BRL) solutions which consists of a single step extraction by guanidinium isothiocyanate and phenol-chloroform.

For Northern blot analysis of GP88 mRNA expression in human cell lines, a 672 bp human GP88 cDNA probe was developed corresponding to nucleotide 1002 to 1674 (corresponding to amino-acid sequence 334–558) of human GP88.

With respect to FIG. 6, C57MG cells were cultivated in the presence of increasing concentrations of GP88 purified from PC cells conditioned medium (top panel), and recombinant GP88 expressed in insect cells (bottom panel), to demonstrate the growth stimulating effect of increasing concentrations of GP88 on the growth of the mouse mammary epithehal cell line C57MG.

A correlation between IGF-1 autocrine production and increased malignancy has also been well established for glioblastomas, teratocarcinomas and breast carcinomas. In these cancers, GP88 expression is also elevated in human tumors when compared to non-tumorigenic human fibroblasts and other human cell lines. GP88 promotes the growth of mammary carcinoma cells.

Anti-GP88 Antibodies

The invention provides compositions for treating and diagnosing diseases linked to increased expression of GP88. This also will apply to treatment and diagnosis of diseases linked to increased responsiveness to GP88. The compositions of this invention include anti-GP88 antibodies which neutralize the biological activity of GP88.

The present invention is also directed to an antibody specific for an epitope of GP88 and the use of such antibody to detect the presence or measure the quantity or concentration of GP88 molecule, a functional derivative thereof or a homologue from different animal species in a cell, a cell or tissue extract, culture medium or biological fluid (e.g., whole blood, serum, plasma, lymph, and urine). Moreover, anti-GP88 antibody can be used to target cytotoxic molecules to a specific site.

For use as antigen for development of antibodies, the GP88 protein naturally produced or expressed in recombinant form or functional derivative thereof, preferably having at least 9 amino-acids, is obtained and used to immunize an animal for production of polyclonal or monoclonal antibody. An antibody is said to be capable of binding a molecule if it is capable of reacting with the molecule to thereby bind the molecule to the antibody. The specific reaction is meant to indicate that the antigen will react in a highly selective manner with its corresponding antibody and not with the multitude of other antibodies which may be evoked by other antigens.

The term antibody herein includes but is not limited to human and non-human polyclonal antibodies, human and non-human monoclonal antibodies (mAbs), chimeric antibodies, anti-idiotypic antibodies (anti-IdAb) and humanized antibodies. Polyclonal antibodies are heterogeneous populations of antibody molecules derived either from sera of animals immunized with an antigen or from chicken eggs. Monoclonal antibodies ("mAbs") are substantially homogeneous populations of antibodies to specific antigens. mAbs may be obtained by methods known to those skilled in the art (U.S. Pat. No. 4,376,110). Such antibodies may be of any immunological class including IgG, IgM, IgE, IgA, IgD and any subclass thereof The hybridoma producing human and non-human antibodies to GP88 may be cultivated in vitro or in vivo. For production of a large amount of mAbs, in vivo is the presently preferred method of production. Briefly, cells from the individual hybridomas are injected intraperitoneally into pristane primed Balb/c mice or Nude mice to produce ascites fluid containing high concentrations of the desired mAbs. mAbs may be purified from such ascites fluids or from culture supernatants using standard chromatography methods well known to those of skill in the art.

Human monoclonal Ab to human GP88 can be prepared by immunizing transgenic mice expressing human immunoglobulin genes. Hybridoma produced by using lymphocytes from these transgenic animals will produce human immunoglobulin instead of mouse immunoglobulin.

Since most monoclonal antibodies are derived from murine source and other non-human sources, their clinical efficiency may be limited due to the immunogenicity of rodent mAbs administered to humans, weak recruitment of effector function and rapid clearance from serum. To circumvent these problems, the antigen-binding properties of murine antibodies can be conferred to human antibodies through a process called humanization. A humanized antibody contains the amino-acid sequences for the 6 complementarity-determining regions (CDRs) of the parent murine nab which are grafted onto a human antibody framework. The low content of non-human sequences in humanized antibodies (around 5%) has proven effective in both reducing the immunogenicity and prolonging the serum half life in humans. Methods such as the ones using monovalent phage display and combinatorial library strategy for humanization of monoclonal antibodies are now widely applied to the humanization of a variety of antibodies and are known to people skilled in the art. These humanized antibodies and human antibodies developed with transgenic animals as described above are of great therapeutic use for several diseases including but not limited to cancer.

Hybridoma supernatants and sera are screened for the presence of, antibody specific for GP88 by any number of immunoassays including dot blots and standard immunoassays (EIA or ELISA) which are well known in the art. Once a supernatant has been identified as having an antibody of interest, it may be further screened by Western blotting to identify the size of the antigen to which the antibody binds. One of ordinary skill in the art will know how to prepare and screen such hybridomas without undue experimentation in order to obtain a desired polyclonal or mAb.

Chimeric antibodies have different portions derived from different animal species. For example, a chimeric antibody might have a variable region from a murine mAb and a human immunoglobulin constant region. Chimeric antibodies and methods for their production are also known to those skilled in the art.

Accordingly, mAbs generated against GP88 may be used to induce human and non-human anti-IdAbs in suitable animals. Spleen cells from such immunized mice are used to produce hybridomas secreting human or non-human anti-Id mAbs. Further, the anti-Id mAbs can be coupled to a carrier such as Keyhole Limpet Hemocyanin (KLH) or bovine serum albumin (BSA) and used to immunize additional mice. Sera from these mice will contain human or non-human anti-anti-IdAb that have the binding properties of the original nab specific for a GP88 polypeptide epitope. The anti-Id mAbs thus have their own idiotypic epitopes or idiotypes structurally similar to the epitope being evaluated.

The term antibody is also meant to include both intact molecules as well as fragments thereof such as, for example, Fab and F(ab')2, which are capable of binding to the antigen. Fab and F(ab')2 fragments lack the Fc fragment of intact antibody, clear more rapidly from the circulation and may have less non-specific tissue binding than an intact antibody. Such fragments are typically produced by proteolytic cleavage, using enzymes such as papain (to generate Fab fragments) and pepsin (to generate F(ab')2 fragments). It will be appreciated that Fab and F(ab')2 and other fragments of the antibodies useful in the present invention may be used for the detection or quantitation of GP88, and for treatment of pathological states related to GP88 expression, according to the methods disclosed herein for intact antibody molecules.

According to the present invention, antibodies that neutralize GP88 activity in vitro can be used to neutralize GP88 activity in vivo to treat diseases associated with increased GP88 expression or increased responsiveness to GP88. A subject, preferably a human subject, suffering from a disease associated with increased GP88 expression is treated with an antibody to GP88. Such treatment may be performed in conjunction with other anti-cancer or anti-viral therapy. A typical regimen comprises administration of an effective amount of the antibody specific for GP88 administered over a period of one or several weeks and including between about one and six months. The antibody of the present invention may be administered by any means that achieves its intended purpose. For example, administration may be by various routes including but not limited to subcutaneous, intravenous, intradermal, intramuscular, intraperitoneal and oral. Parenteral administration can be by bolus injection or by gradual perfusion over time. Preparations for parenteral administration include sterile aqueous or non-aqueous solutions, suspensions and emulsions, which may contain auxiliary agents or recipients known in the art. Pharmaceutical compositions such as tablets and capsules can also be prepared according to routine methods. It is understood that the dosage of will be dependent upon the age, sex and weight of the recipient, kind of concurrent treatment, if any, frequency of treatment and the nature of the effect desired. The ranges of effective doses provided below are not intended to limit the invention and merely represent preferred dose ranges. However the most preferred dosage will be tailored to the individual subject as is understood and determinable by one skilled in the art. The total dose required for each treatment may be administered by multiple doses or in a single dose. Effective amounts of antibody are from about 0.01 µg to about 100 mg/kg body weight and preferably from about 10 µg to about 50 mg/kg. Antibody may be administered alone or in conjunction with other therapeutics directed to the same disease.

According to the present invention and concerning the neutralizing antibody, GP88 neutralizing antibodies can be used in all therapeutic cases where it is necessary to inhibit GP88 biological activity, even though there may not necessarily be a change in GP88 expression, including cases where there is an overexpression of GP88 cell surface receptors and this in turn results in an increased biological activity, or where there is an alteration in GP88 signaling pathways or receptors leading to the fact that the signaling pathways are always "turned on." Neutralizing antibodies to growth factor and to growth factor receptors have been successfully used to inhibit the growth of cells whose proliferation is dependent on this growth factor. This has been the case for IGF-I receptor in human breast carcinoma cells and bombesin for lung cancer. The antibody to GP88 can also be used to deliver compounds such as, but not limited to, cytotoxic reagents such as toxins, oncotoxins, mitotoxins and immunotoxins, or antisense oligonucleotides, in order to specifically target them to cells expressing or responsive to GP88.

One region that allows antigen to develop a neutralizing antibody to GP88 is the 19 amino-acid region defined as K19T in the mouse GP88, and E19V in the human GP88 which is not located within the epithelin/granulin 6 kDa repeats but between these repeats, specifically between granulin A (epithelin 1) and granulin C in what is considered a variant region (see FIG. 10). Without wishing to be bound by theory, it is believed that the region important for the biological activity of GP88 lies outside of the epithelin repeats.

The antibodies or fragments of antibodies useful in the present invention may also be used to quantitatively or qualitatively detect the presence of cells which express the GP88 protein. This can be accomplished by immunofluorescence techniques employing a fluorescently labeled antibody (see below) with fluorescent microscopic, flow cytometric, or fluorometric detection. The reaction of antibodies and polypeptides of the present invention may be detected by immunoassay methods well known in the art.

The antibodies of the present invention may be employed histologically as in light microscopy, immunofluorescence or immunoelectron microscopy, for in situ detection of the GP88 protein in tissues samples, biopsies, and biological fluids. In situ detection may be accomplished by removing a histological specimen from a patient and applying the appropriately labeled antibody of the present invention. The antibody (or fragment) is preferably provided by applying or overlaying the labeled antibody (or fragment) to the biological sample. Through the use of such a procedure, it is possible to determine not only the presence of the GP88 protein but also its distribution in the examined tissue or concentration in a biological fluid. Using the present invention, those of ordinary skill in the art will readily perceive that any wide variety of histological methods (such as staining procedures) can be modified in order to achieve such in situ detection.

Assays for GP88 typically comprise incubating a biological sample such as a biological fluid, a tissue extract, freshly harvested or cultured cells or their culture medium in the presence of a detectably labeled antibody capable of identifying the GP88 protein and detecting the antibody by any of a number of techniques well known in the art.

The biological sample may be treated with a solid phase support or carrier such as nitrocellulose or other solid support capable of immobilizing cells or cell particles or soluble proteins. The support may then be washed followed by treatment with the detectably labeled anti-GP88 antibody. This is followed by wash of the support to remove unbound antibody. The amount of bound label on said support may then be detected by conventional means. By solid phase support is intended any support capable of binding antigen or antibodies such as but not limited to glass, polystyrene polypropylene, nylon, modified cellulose, or polyacrylamide.

The binding activity of a given lot of antibody to the GP88 protein may be determined according to well known methods. Those skilled in the art will be able to determine operative and optimal assay conditions for each determination by employing routine experimentation.

Detection of the GP88 protein or functional derivative thereof and of a specific antibody for the protein may be accomplished by a variety of immunoassays well known in the art such as enzyme linked immunoassays (EIA) or radioimmunoassays (RIA). Such assays are well known in the art and one of skill will readily know how to carry out such assays using the anti-GP88 antibodies and GP88 protein of the present invention.

Such immunoassays are useful to detect and quantitate GP88 protein in serum or other biological fluid as well as in tissues, cells, cell extracts, or biopsies. In a preferred embodiment, the concentration of GP88 is measured in a tissue specimen as a means for diagnosing cancer or other disease associated with increased expression of GP88. In another preferred embodiment, the concentration of GP88 in a biological fluid sample is used to determine if a patient is likely to be responsive, or is responding to, anti-tumorigenic therapy.

The presence of certain types of cancers (e.g., breast cancer) and the degree of malignancy are said to be "proportional" to an increase in the level of the GP88 protein. The term "proportional" as used herein is not intended to be limited to a linear or constant relationship between the level of protein and the malignant properties of the cancer. The term "proportional" as used herein, is intended to indicate that an increased level of GP88 protein is related to appearance, recurrence or display of malignant properties of a cancer or other disease associated with increased expression of GP88 at ranges of concentration of the protein that can be readily determined by one skilled in the art.

Another embodiment of the invention relates to evaluating the efficacy of anti-cancer or anti-viral drug or agent by measuring the ability of the drug or agent to inhibit the expression or production of GP88. The antibodies of the present invention are useful in a method for evaluating anti-cancer or anti-viral drugs in that they can be employed to determine the amount of the GP88 protein in one of the above-mentioned immunoassays. Alternatively, the amount of the GP88 protein produced is measured by bioassay (cell proliferation assay) as described herein. The bioassay and immunoassay can be used in combination for a more precise assessment.

An additional embodiment is directed to an assay for diagnosing cancers or other diseases associated with an increase in GP88 expression based on measuring in a tissue or biological fluid the amount of mRNA sequences present that encode GP88 or a functional derivative thereof, preferably using an RNA-DNA hybridization assay. The presence of certain cancers and the degree of malignancy is proportional to the amount of such mRNA present. For such assays the source of mRNA will be biopsies and surrounding tissues. The preferred technique for measuring the amount of mRNA is a hybridization assay using DNA of complementarity base sequence.

Another related embodiment is directed to an assay for diagnosing cancers or other diseases associated with an increase in GP88 responsiveness based on measuring on a tissue biopsy whether treatment with anti-GP88 neutralizing antibody will inhibit its growth or other biological activity.

Another related embodiment is a method for measuring the efficacy of anti-cancer or anti-viral drug or agent which comprises the steps of measuring the agent's effect on inhibiting the expression of mRNA for GP88. Similarly such method can be used to identify or evaluate the efficacy of GP88 antagonizing agents by measuring the ability of said agent to inhibit the production of GP88 mRNA.

Nucleic acid detection assays, especially hybridization assays, can be based on any characteristic of the nucleic acid molecule such as its size, sequence, or susceptibility to digestion by restriction endonucleases. The sensitivity of such assays can be increased by altering the manner in which detection is reported or signaled to the observer. A wide variety of labels have been extensively developed and used by those of ordinary skill in the art, including enzymatic, radioisotopic, fluorescent, chemical labels and modified bases.

One method for overcoming the sensitivity limitation of a nucleic acid for detection is to selectively amplify the nucleic acid prior to performing the assay. This method has been referred as the "polymerase chain reaction" or PCR (U.S. Pat. Nos. 4,683,202 and 4,582,788). The PCR reaction provides a method for selectively increasing the concentration of a particular nucleic acid sequence even when that sequence has not been previously purified and is present only in a single copy in a particular sample.

Detection of GP88 in Biological Fluids

Preferred embodiments of the invention are directed to methods and kits for detecting GP88 in biological fluids. As described above, cancer cells express elevated levels of GP88. The present invention demonstrates that GP88 can be detected in biological fluids at a concentration as low as about 0.1 ng/ml. As described above, GP88 is overexpressed in cancer cells and elevated levels of GP88 are indicative of tumorigenicity. Typically, a tissue sample or biopsy is required to detect the presence of a tumor marker. For example, breast cancer patients are often subjected to needle biopsy procedures in order to remove samples of breast tissue for examination to determine whether a particular tumor marker is present. Biopsy procedures, like any surgical procedure, are associated with increased risk to the patient. Biopsy procedures, in particular, have been associated with increased risk of tumor formation.

Unlike tissue biopsy procedures, blood sampling is a routine and safe procedure that can be carried out by a patient if necessary. For example, a small sterile lance can be used to prick a patient's fingertip and obtain a small sample of blood. The blood sample can be processed by any suitable procedure to isolate the serum or plasma fractions. Alternatively, a whole blood sample can be used. An assay, for example an enzyme-linked immunoabsorption assay (ELISA), utilizing anti-GP88 antibodies can be used to detect the presence and quantitate the amount of GP88 in the serum sample. Blood sampling avoids the risks associated with tissue biopsies. In addition, obtaining blood samples from the same patient on a regular basis (e.g., weekly examinations) permits monitoring of the patient to determine the level of GP88 in the serum over time. If the level of GP88 increases, the physician can treat the patient accordingly (e.g., administering GP88 antagonists) before significant tumor growth can occur.

In carrying out a method of measuring the concentration of GP88 in a biological fluid, a biological fluid (e.g., whole blood, plasma, serum, lymph, saliva, and urine) is contacted with an anti-GP88 antibody and the concentration of GP88 is measured. GP88 can be detected, for example, at a concentration as low as about 0.1 ng/ml. In another embodiment of the invention, GP88 can be detected at a concentration of at least about 10 ng/ml of biological fluid. As described above, anti-GP88 antibodies can bind to GP88 and be used to determine the amount of GP88 in a sample. Examples of anti-GP88 antibodies that can be used to measure the concentration of GP88 in a biological fluid sample include, but are not limited to, antibodies produced from the following hybridoma cell lines ATCC Accession No. PTA-5262 (6B3) and PTA-5261 (6b2) (American Type Culture Collection, 10801 University Blvd., Manassas, Va. 20110).

ELISAs are rapid, sensitive, and reproducible assays for quantifying the amount of an antigen in a sample. A "sandwich" ELISA utilizes a primary antibody to bind to or "capture" its antigen (e.g., a protein) and a labeled secondary antibody to also bind to the antigen. The addition of a substrate for the detection moiety results in a signal (e.g., color change, or radioactivity) that is proportional to the amount of antigen present in the sample. In an exemplary sandwich ELISA, the primary antibody is adsorbed to a support such as a well of a microtiter plate. A sample containing the antigen is incubated with the attached primary antibody and the antigen is permitted to bind to the antibody. Next, a secondary antibody labeled with a detection molecule (e.g., enzyme, radionuclide) is also permitted to bind to the antigen. Examples of labels include alkaline phosphatase and horseradish peroxidase. Alternatively, the secondary antibody is unlabeled and a third antibody (e.g., a labeled anti-IgG antibody) is also used in the assay. The labeled third antibody binds to the constant region of immunoglobulin G (IgG). The addition of a substrate for the enzyme (e.g., 2,2-azo-bis(3-ethylbenzthiazoline-6-sulfonic acid) (ABTS), o-phenylenediamine (OPD), and 3,3,-5,5-tetramethylbenzidine base (TMB)) results in a color change in the sample solution that is proportional to the amount of antigen present in the sample. The color change can be detected using a spectrophotometer at a wavelength suitable for detecting the color change induced by the enzyme label (e.g., 624 nm using TMB as a substrate).

Alternatively, the secondary antibody or third antibody can be labeled with a radioactive moiety (e.g., $^{125}$I, $^{35}$S, $^{32}$P, $^{12}$C). A radioactivity detector (e.g., gamma counter) can be used to measure the radioactivity emitted by the secondary antibody after binding to the antigen. The level of radioactivity is proportional to the amount of antigen present in the sample. In yet another alternative, the level of GP88 in a biological fluid sample can be determined using a Western blot procedure. In an exemplary Western blot procedure, the biological fluid sample is loaded on to an SDS Polyacrylamide Gel (SDS-PAGE) which is subjected to an electric current (e.g., 20 mA) to separate the proteins in the biological fluid sample by molecular weight. The proteins are transferred to a nitrocellulose membrane and incubated with a labeled anti-GP88 antibody. If the anti-GP88 antibody is labeled with an enzyme, the nitrocellulose membrane is exposed to the substrate for the enzyme which induces a color change in the GP88 protein band located on the nitrocellulose membrane. The amount of GP88 in the sample is proportional to the degree of color change.

In one embodiment of the invention, GP88 monoclonal antibody 6B3, produced by hybridoma cell line (ATCC Number PTA-5262) is used as the primary antibody in a sandwich ELISA. Various antibodies raised against GP88 can be used in an ELISA to detect GP88 (e.g., GP88 monoclonal antibodies 6B3, 6B2, 2A5, 4D1, 3F5, 5B4, 3F8 produced from following hybridoma cell lines respectively ATCC Number PTA-5262, ATCC Number PTA-5261, ATCC Number PTA-5589, ATCC Number PTA-5593, ATCC Number PTA-5259, ATCC Number PTA-5260, ATCC Number PTA-5591. Hybridoma cell lines ATCC Number PTA-5262, ATCC Number PTA-5261, and ATCC Number PTA-5259 were deposited on Jun. 18, 2003, with American Type Culture Collection, located at 10801 University Blvd., Manassas, Va., 20110. Hybridoma cell lines ATCC Number PTA-5589, ATCC Number PTA-5593, ATCC Number PTA-5260, and ATCC Number PTA-5591 were deposited on Oct. 17, 2003, with American Type Culture Collection.). GP88 antibodies labeled with horseradish peroxidase can be used as the secondary antibody, and TMB can be used as the substrate. Alternatively, a labeled antibody capable of binding the constant region of an immunoglobulin can be used as the secondary antibody in an ELISA. (e.g., anti-IgG antibody). Samples containing known quantities of GP88 protein (0.1, 2, 5, 10, 20 nanograms) in a carrier (e.g., buffer solution) can be used to generate a standard curve based on the results of an ELISA. The optical density of the sample can be plotted against the known amount of GP88 in the sample to generate a standard curve (e.g., FIG. 16). The concentration of GP88 in an unknown sample can be determined by measuring the optical density of an unknown sample and using the standard curve to calculate the GP88 concentration.

An exemplary protocol for a sandwich ELISA includes the following steps:

(1) Add a solution containing the primary antibody to the bottom of the well of a microtiter plate (e.g., 50 microliters of an antibody solution containing 20 mg/ml of antibody).

(2) incubate the microtiter plate overnight at 4° C. to allow for complete binding of the antibody to the well.

(3) wash the wells with a buffer solution (e.g., phosobuffered saline (PBS))

(4) block non-specific protein binding by saturating the wells with a blocking buffer (e.g., Bovine Serum Albumin (BSA) in PBS)

(5) wash the wells with a buffer solution (6) add a solution containing the antigen and incubate the microtiter plate at room temperature for at least 2 hours.

(7) wash the wells with a buffer solution (8) add the labeled secondary antibody and incubate the microtiter plate for at least two hours at room temperature (9) wash the wells with a buffer solution

(10) add the desired substrate diluted in a buffer solution, allow sufficient time for a reaction to occur

(11) read the optical density of resulting substrate solution in an ELISA reader at the appropriate wavelength for the substrate.

Figure 16:
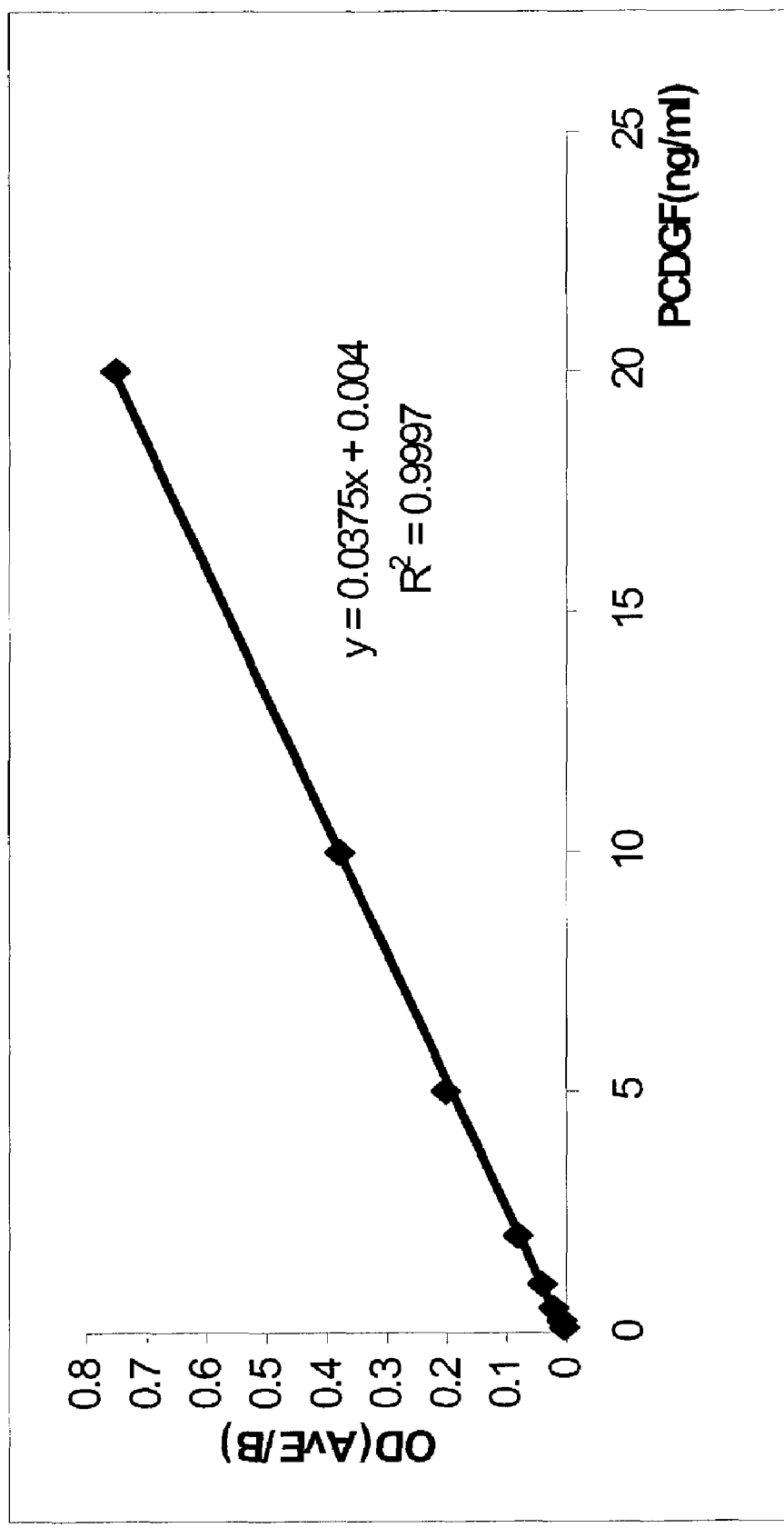
FIG. 16 is a graph showing the optical density (y-axis) of serum samples containing known quantities of GP88 (x-axis). The graph can be used as a reference to determine the concentration of GP88 in a biological fluid sample such as blood serum.

FIG. 16 shows an exemplary curve that can be used for determining the concentration of GP88 in a blood serum biological fluid. Samples containing known quantities of recombinant GP88 protein were prepared and measured using an ELISA assay. The optical densities of the samples were plotted against known quantities of GP88 protein. FIG. 16 shows a linear relationship between the OD (optical density) of a biological fluid sample (y-axis) and the concentration of GP88 (x-axis). The concentration of GP88 in a biological fluid sample can be determined by using anti-GP88 antibodies in a suitable detection technique (e.g., ELISA, RIA, Western blot) as described above. In one embodiment, the optical density of the biological fluid sample is measured and the concentration of GP88 in the biological fluid sample is determined by comparing the measured optical density to a standard curve (e.g., FIG. 16). For example, using the curve of FIG. 16, if the optical density of a biological fluid sample contacted with anti-GP88 antibody and subjected to an immunoassay is 0.6, the concentration of GP88 in the biological fluid sample would be 15 ng/ml.

Serum concentrations of GP88 in healthy humans vary between about 23 ng/ml and 44 ng/ml in healthy humans. Measurement of the level of GP88 in plasma from healthy human volunteers gave similar results. Human breast cancer patients showed elevated levels of GP88 in serum. Three out of twenty breast cancer patients showed elevated levels of GP88 (49, 51, and 56 ng/ml). However, patients with progressive disease (e.g., metastatic) who showed no response to therapy had dramatically increased serum levels of GP88 over time (from 27 to 233 ng/ml in 6 months). Another patient with advanced disease who was non-responsive to anti-tumorigenic therapy had a GP88 serum concentration of 158 ng/ml on Mar. 21, 2002 and 148 ng/ml on May 23, 2002. Patients initially diagnosed with non-metastatic breast cancer and patients in remission had GP88 serum concentrations within the normal range. Thus, elevated serum concentrations of GP88 (e.g., about 40 to 50 ng/ml) are indicative of tumorigenicity. Highly elevated levels of serum GP88 (e.g., about 100 to 300 ng/ml) are indicative of progressive disease and resistance to anti-tumorigenic therapy.

In another embodiment of the invention, a method of diagnosing tumorigenicity is provided comprising measuring the level of GP88 protein in a first biological fluid sample, measuring the level of GP88 protein in a second biological fluid sample, and diagnosing tumorigenicity by determining whether the measured level of GP88 protein in the second biological fluid sample is higher than the level of GP88 protein in the initial biological fluid sample by an amount sufficient to indicate tumorigenicity. An initial biological fluid sample can be taken from a patient suspected of having cancer or cell growth-related disease. The level of GP88 in the initial biological fluid sample can be measured and compared to the level of GP88 in a second biological fluid sample taken at a different time. Biological fluid samples can be taken at regular intervals and the measured concentration of GP88 in subsequent samples can be compared to the GP88 level in the initial sample. If the results indicate an increase in the level of GP88 in the biological fluid over time, the physician can initiate or modify the patient's treatment in order to reduce or eliminate tumor growth.

The invention also provides methods of determining whether a patient is responsive or responding to anti-tumorigenic therapy comprising measuring the concentration of GP88 in a biological fluid sample from a patient receiving anti-tumorigenic therapy, wherein a concentration of GP88 of at least about 100 ng/ml indicates that the patient is not responding to anti-tumorigenic therapy. The term "anti-tumorigenic therapy" refers to any medicament, drug, therapy, or method of administering a medicament, drug, or therapy for the purpose of treating cancer or a growth-related disease. Examples of anti-tumorigenic therapy include antiestrogen therapy, the use of anti-tumor antibodies (e.g., anti-GP88 antibodies), antisense therapy (e.g., anti-GP88 nucleic acids), chemotherapy, radiation treatment, and gene therapy. The GP88 serum concentration of a patient undergoing anti-tumorigenic therapy can be monitored by analyzing serum samples at regular intervals (e.g., daily, weekly, monthly). A GP88 serum level of at least about 100 ng/ml can indicate that the patient will not be responsive to or is not responding to, anti-tumorigenic therapy.

Certain anti-tumorigenic therapies pose undesirable side effects or additional risk to a patient. For example, treatment or prevention of breast cancer with antiestrogens (e.g., tamoxifen, raloxifene) is associated with increased risk of ovarian cancer. Elevated levels of GP88 indicate that a patient will not be responsive to treatment with antiestrogens. If a patient has elevated levels of GP88 (e.g., greater than about 100 ng/ml), the patient would likely not be responsive to antiestrogen therapy and the additional risk posed by antiestrogen therapy may outweigh any benefit. Chemotherapy also is associated with many undesirable side effects including, nausea, weakness, hair loss, appetite loss etc. If a patient is not likely to respond to a particular type of chemotherapy, an anti-tumorigenic therapy with fewer side effects may be more effective and not subject the patient to additional trauma. The present invention is useful for determining if a patient will be responsive or is responding to antitumorigenic therapy.

Another embodiment of the invention provides methods of treating or preventing re-occurrence of cancer in a patient by determining the concentration of GP88 in a biological fluid sample, and administering anti-tumorigenic therapy in an amount sufficient to treat or prevent the cancer if the concentration of GP88 in said biological fluid sample is about 40 to 50 ng/ml. As described above and shown, patients with GP88 serum levels of about 40 ng/ml or higher either have been diagnosed with cancer or have a significantly higher risk of developing cancer. Anti-tumorigenic therapy (e.g., antiestrogen therapy, anti-tumor antibody therapy, antisense therapy, chemotherapy, radiation treatment, and gene therapy) can be administered to patients diagnosed with cancer or at an elevated risk of developing cancer to prevent or treat the disease.

Antiestrogen therapy relates to administration of antiestrogens for the purpose of preventing or treating tumor growth. Examples of antiestrogens include tamoxifen and raloxifene. Tamoxifen citrate ("tamoxifen") is a nonsteroidal antiestrogen commonly prescribed to patients suffering from breast cancer that has demonstrated potent antiestrogenic and antineoplastic properties. See U.S. Pat. No. 4,536,516. Tamoxifen is an estrogen receptor antagonist that competes with estrogen for binding to estrogen receptors. Other antiestrogens include, raloxifene, aromatase inhibitors (e.g., Arimidex® (anastrozole), Femera®), and estrogen receptor down-regulators (e.g., Faslodex®). The antiestrogenic effects of tamoxifen may be related to its ability to compete with estrogen for binding sites in target tissues. Other antiestrogens, such as aromatase inhibitors, inhibit or reduce the amount of estrogen available.

Anti-tumor antibodies (e.g., anti-GP88 antibodies, herceptin) can be administered to a patient to inhibit the activity of tumor initiating or promoting proteins or other molecules. For example, anti-GP88 antibodies can be administered to inhibit the activity of GP88. Anti-tumor antibodies can be administered to a patient by a variety of routes (oral, injection, parenteral) as described above.

Antisense therapy refers to administration of antisense nucleic acids to a patient to inhibit the replication of tumor promoting genes or inhibit the translation of tumor promoting proteins. Examples of antisense therapy include the administration of anti-GP88 antisense nucleic acids. Antisense nucleic acids can be administered by direct injection into tissue, intravenously, or parenterally. Antisense nucleic acids can also be administered to cells using ex vivo techniques. Tumorigenic or normal cells can be removed from a subject (e.g., human, dog, cow, goat, mouse, rat, rabbit, horse, or chicken) and grown in culture. The cells can be transfected with DNA or RNA encoding antisense nucleic acids, re-introduced into the subject, and produce antisense nucleic acids to inhibit tumor cell proliferation.

"Gene therapy" refers to administration of a nucleic acid encoding an anti-tumor protein to a patient to prevent or treat tumor growth. As with antisense nucleic acids, gene therapy nucleic acids can be administered by direct injection or using the ex vivo techniques described above. Cell transfected with gene therapy nucleic acids can produce anti-tumor proteins to inhibit or prevent tumor growth.

Chemotherapy refers generally to treatment of cancer using chemical compounds or combinations of chemical compounds (e.g., methotrexate, [insert others]). The particular combination of chemotherapeutic agents will depend on the particular tumor type and the stage of the disease. Radiation therapy refers to the use of radiation (e.g., gamma radiation) to directly kill tumor cells. The amount and type of radiation used will also depend on the particular tumor type and the stage of the disease.

The invention also provide kits for diagnosing tumorigenicity and determining whether a patient is responsive or responding to anti-tumorigenic therapy. Such kits preferably comprise a container and a compound or compounds for detecting GP88 (e.g., anti-GP88 antibodies or antibody fragments). The anti-GP88 antibody or antibody fragment can be labeled (e.g., enzymatic, radioisotopic, fluorescent, and chemical labels) for use in a suitable detection method (e.g., ELISA, radioimmunoassay). In one embodiment, the kits contain at least one primary antibody (e.g., anti-GP88 monoclonal antibody 6B3), at least one labeled secondary antibody (e.g., anti-human GP88 polyclonal antibody labeled with a detection enzyme such as HRP), and at least one substrate (e.g., TMB). Alternatively, the kits can contain radiolabeled secondary antibody in place of the secondary antibody labeled with an enzyme. The kits may also contain disposable supplies for carrying out detection assays (e.g., microtiter plates, pipettes).

GP88 Antisense Components

This invention also provides GP88 antisense components. The constitutive expression of antisense RNA in cells has been shown to inhibit the expression of more than 20 genes and the list continues to grow. Possible mechanisms for antisense effects are the blockage of translation or prevention of splicing, both of which have been observed in vitro. Interference with splicing allows the use of intron sequences which should be less conserved and therefore result in greater specificity, inhibiting expression of a gene product of one species but not its homologue in another species.

The term antisense component corresponds to an RNA sequence as well as a DNA sequence coding therefor, which is sufficiently complementary to a particular mRNA molecule, for which the antisense RNA is specific, to cause molecular hybridization between the antisense RNA and the mRNA such that translation of the mRNA is inhibited. Such hybridization can occur under in vivo conditions. The action of the antisense RNA results in specific inhibition of gene expression in the cells.

According to the present invention, transfection of multiple myeloma cells with DNA antisense to the GP88 cDNA inhibits endogenous GP88 expression and inhibits tumorigenicity of the antisense cDNA transfected cells. This antisense DNA must have sufficient complementarity, about 18–30 nucleotides in length, to the GP88 gene so that the antisense RNA can hybridize to the GP88 gene (or mRNA) and inhibit GP88 gene expression regardless of whether the action is at the level of splicing, transcription, or translation. The degree of inhibition is readily discernible to one skilled in the art without undue experimentation given the teachings herein and preferably is sufficient to inhibit the growth of cells whose proliferation is dependent on the expression of GP88. One of ordinary skill in the art will recognize that the antisense RNA approach is but a number of known mechanisms which can be employed to block specific gene expression.

The antisense components of the present invention may be hybridizable to any of several portions of the target GP88 cDNA, including the coding sequence, 3' or 5' untranslated regions, or other intronic sequences, or to GP88 mRNA. As is readily discernible by one of ordinary skill in the art, the minimal amount of homology required by the present invention is that sufficient to result in hybridization to the GP88 DNA or mRNA and in inhibition of transcription of the DNA, or translation or function of the mRNA, preferably without affecting the function of other mRNA molecules and the expression of other unrelated genes.

Antisense RNA is delivered to a cell by transformation or transfection via a vector, including retroviral vectors and plasmids, into which has been placed DNA encoding the antisense RNA with the appropriate regulatory sequences including a promoter to result in expression of the antisense RNA in a host cell. Stable transfection of various antisense expression vectors containing GP88 cDNA fragments in the antisense orientation have been performed. One can also deliver antisense components to cells using a retroviral vector. Delivery can also be achieved by liposomes.

For purpose of antisense technology for in vivo therapy, the currently preferred method is to use antisense oligonucleotides, instead of performing stable transfection of an antisense cDNA fragment constructed into an expression vector. Antisense oligonucleotides having a size of 15–30 bases in length and with sequences hybridizable to any of several portions of the target GP88 cDNA, including the coding sequence, 3' or 5' untranslated regions, or other intronic sequences, or to GP88 mRNA, are preferred. Sequences for the antisense oligonucleotides to GP88 are preferably selected as being the ones that have the most potent antisense effects. Factors that govern a target site for the antisense oligonucleotide sequence are related to the length of the oligonucleotide, binding affinity, and accessibility of the target sequence. Sequences may be screened in vitro for potency of their antisense activity by measuring inhibition of GP88 protein translation and GP88 related phenotype, e.g., inhibition of cell proliferation in cells in culture. In general it is known that most regions of the RNA (5' and 3' untranslated regions, AUG initiation, coding, splice junctions and introns) can be targeted using antisense oligonucleotides.

The preferred GP88 antisense oligonucleotides are those oligonucleotides which are stable, have a high resilience to nucleases (enzymes that could potentially degrade oligonucleotides), possess suitable pharmacokinetics to allow them to traffic to disease tissue at non-toxic doses, and have the ability to cross through plasma membranes.

Phosphorothioate antisense oligonucleotides may be used. Modifications of the phosphodiester linkage as well as of the heterocycle or the sugar may provide an increase in efficiency. With respect to modification of the phosphodiester linkage, phophorothioate may be used. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo. Cell culture and in vivo tumor experiments using these types of oligonucleotides targeted to c-raf-1 resulted in enhanced potency.

The delivery route will be the one that provides the best antisense effect as measured according to the criteria described above. In vitro cell culture assays and in vivo tumor growth assays using antisense oligonucleotides have shown that delivery mediated by cationic liposomes, by retroviral vectors and direct delivery are efficient. Another possible delivery mode is targeting using antibody to cell surface markers for the tumor cells. Antibody to GP88 or to its receptor may serve this purpose.

Recombinant GP88

The present invention is also directed to DNA expression systems for expressing a recombinant GP88 polypeptide or a functional derivative thereof substantially free of other mammalian DNA sequences. Such DNA may be double or single stranded. The DNA sequence should preferably have about 20 or more nucleotides to allow hybridization to another polynucleotide. In order to achieve higher specificity of hybridization, characterized by the absence of hybridization to sequences other than those encoding the GP88 protein or a homologue or functional derivative thereof, a length of at least 50 nucleotides is preferred.

The present invention is also directed to the above DNA molecules, expressible vehicles or vectors as well as hosts transfected or transformed with the vehicles and capable of expressing the polypeptide. Such hosts may be prokaryotic, preferably bacteria, or eukaryotic, preferably yeast or mammalian cells. A preferred vector system includes baculovirus expressed in insect cells. The DNA can be incorporated into host organisms by transformation, transduction, transfection, infection or related processes known in the art. In addition to DNA and mRNA sequences encoding the GP88 polypeptide, the invention also provides methods for expression of the nucleic acid sequence. Further, the genetic sequences and oligonucleotides allow identification and cloning of additional polypeptides having sequence homology to the polypeptide GP88 described here.

An expression vector is a vector which (due to the presence of appropriate transcriptional and/or translational control sequences) is capable of expressing a DNA (or cDNA) molecule which has been cloned into the vector and thereby produces a polypeptide or protein. Expression of the cloned sequence occurs when the expression vector is introduced into an appropriate host cell. If a prokaryotic expression vector is employed, then the appropriate host cell would be any prokaryotic cell capable of expressing the cloned sequence. Similarly, if an eukaryotic expression system is employed, then the appropriate host cell would be any eukaryotic cell capable of expressing the cloned sequence. Baculovirus vector, for example, can be used to clone GP88 cDNA and subsequently express the cDNA in insect cells.

A DNA sequence encoding GP88 polypeptide or its functional derivatives may be recombined with vector DNA in accordance with conventional techniques including blunt-ended or staggered ended termini for ligation, restriction enzyme digestion to provide appropriate termini, filling in cohesive ends as appropriate, alkaline phosphatase treatment to avoid undesirable joining, and ligation with proper enzyme ligases. Techniques for such manipulations are discussed in (35).

A nucleic acid molecule is capable of expressing a polypeptide if it contains nucleotide sequences which contain transcriptional and translational regulatory information and such sequences are operably linked to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism but shall in general include a promoter region, which in prokaryotes contains both the promoter (which directs the initiation of RNA transcription) as well as the DNA sequences which when transcribed into RNA will signal the initiation of protein synthesis. Such regions will normally include those 5' non-coding sequences involved with the initiation of transcription, translation such as the TATA box, capping sequence, CAAT sequence and the like.

If desired, the 3' non-coding region to the gene sequence encoding the protein may be obtained by described methods (screening appropriate cDNA library or PCR amplification). This region may be retained for the presence of transcriptional termination regulatory sequences such as termination and polyadenylation. Thus, by retaining the 3' region naturally contiguous to the DNA sequence coding for the protein, the transcriptional termination signals may be provided.

Where the transcription termination signals are not provided or satisfactorily functional in the expression host cells, then a 3' region from another gene may be substituted.

Two DNA sequences such as a promoter region sequence and GP88 encoding sequence are said to be operably linked if the nature of the linkage between the sequences does not result in the introduction of a frame-shift mutation or interfere with the ability of the promoter sequence to direct transcription of the polypeptide gene sequence. The promoter sequences may be prokaryotic, eukaryotic or viral. Suitable promoters are inducible, repressible or constitutive.

Eukaryotic promoters include but are not limited to the promoter for the mouse methallothionein I gene, the TK promoter of Herpes Virus, the gene gal4 promoter, the SV40 early promoter, the mouse mammary tumor virus (MMTV) promoter, and the cytomegalovirus (CMV) promoter. Strong promoters are preferred. Examples of such promoters are those which recognize the T3, SP6 and T7 polymerases, the PL promoter of bacteriophage lambda, the recA promoter, the promoter of the mouse methallothionein I gene, the SV40 promoter and the CMV promoter.

It is to be understood that application of the teachings of the present invention to a specific problem or environment will be within the capability of one having ordinary skill in the art in light of the teachings contained herein. The present invention is more fully illustrated by the following non-limiting example.

EXAMPLE 1

Determining the Concentration of GP88 in a Biological Fluid Sample

Serum samples were obtained from 17 normal, healthy, human volunteers. GP88 concentrations in human serum samples were measured in triplicate by enzyme-linked immunoabsorbance assay (ELISA). Standard GP88 samples were prepared from recombinant GP88 diluted in a solution of 30% glycerol and 1% milk-PBS at concentrations of 0, 0.1, 0.25, 0.5, 1, 3, 10, and 20 ng/ml. 100 microliter wells on a microtiter plate were coated with 10 microgram per milliliter of anti-human GP88 monoclonal antibody 6B3 (0.78 mg/ml of 6B3 antibody in phospho buffered saline (PBS)) and incubated overnight at 4° C. The wells were washed with PBS followed by the addition of anti-human PCDGF polyclonal (IgG fraction) to each well at a concentration of 3 micrograms/ml at 37° C. for 1.5 hours. The wells were washed in PBS before the addition of detection antibody (horseradish peroxidase (HRP)-goat-rabbit-IgG) to each well. TMB (substrate) was added and allowed to incubate with the samples for 1 hour. The optical density of the samples was determined using an ELISA spectrometer reader set at a wavelength of 620 nanometer. Plotting the optical density of the standard GP88 samples (y-axis) against the amount of GP88 in each sample (x-axis) generated a standard curve (FIG. 16). The GP88 concentration of the unknown samples was determined by measuring the optical density and using the standard curve (FIG. 16) to determine the GP88 concentration. Table 1 provides the GP88 serum sample concentration for each of the seventeen healthy human volunteers:

TABLE 1

| Patient # | GP88 Conc.(ng/ml) |
| --- | --- |
| 1 | 36.415 |
| 2 | 31.534 |
| 3 | 42.342 |
| 4 | 27.109 |
| 5 | 37.85 |
| 6 | 23.793 |
| 7 | 32.837 |
| 8 | 42.208 |
| 9 | 32.089 |
| 10 | 42.792 |
| 11 | 36.213 |
| 12 | 31.902 |
| 13 | 26.383 |
| 14 | 32.823 |
| 15 | 28.028 |
| 16 | 34.1 |

Table 2 shows the GP88 concentration of serum samples taken from a patient with advanced, progressive breast cancer who did not respond to anti-tumorigenic therapy. The GP88 serum concentration increased from 27 to 233 ng/ml in a six-month period.

TABLE 2

| Date | GP88 Conc.(ng/ml) |
| --- | --- |
| Aug. 1, 2001 | 27 |
| Oct. 10, 2001 | 128.26 |
| Mar. 21, 2002 | 233 |

What is claimed as new and desired to be protected by Letters Patent of the United States is:

1. A sensitive method of measuring the concentration of GP88 in a biological fluid comprising contacting a biological fluid with an anti-GP88 antibody or antibody fragment and measuring the concentration of GP88 wherein GP88 is capable of being detected at a concentration as low as about 0.1 to about 10 nanograms of GP88 per milliliter.

2. The method of claim 1, wherein GP88 can be detected at a concentration as low as about 0.1 nanograms of GP88 per milliliter.

3. The method of claim 1, wherein said biological fluid is selected from the group consisting of whole blood, plasma, serum, lymph, saliva, and urine.

4. The method of claim 1, wherein said GP88 antibody is produced from a hybridoma cell line selected from the group consisting of ATCC Accession Number PTA-5262 and ATCC Accession Number PTA-5261.

5. The method of claim 1, wherein said concentration of GP88 is measured by an immunoassay.

6. The method according to claim 1 wherein said anti-GP88 antibody or antibody fragment is derived from an animal immunized with a composition comprising a peptide consisting essentially of SEQ ID NO: 3.

7. The method according to claim 1 wherein said anti-GP88 antibody or antibody fragment is derived from an animal immunized with a composition comprising a peptide consisting essentially of SEQ ID NO: 4.

8. The method according to claim 1 wherein said anti-GP88 antibody or antibody fragment is derived from an animal immunized with a composition comprising a peptide consisting essentially of SEQ ID NO: 5.

9. The method according to claim 1 wherein said anti-GP88 antibody or antibody fragment is derived from an animal immunized with a composition comprising a peptide consisting essentially of SEQ ID NO: 6.

10. The method according to claim 1, wherein said anti-GP88 antibody or antibody fragment is derived from an animal immunized with a composition comprising a peptide consisting essentially of SEQ ID NO: 7.

11. The method according to claim 1, wherein said anti-GP88 antibody is a monoclonal antibody.

12. The method according to claim 1, wherein said anti-GP88 antibody is labeled with a label selected from the group consisting of enzymatic, fluorescent, and radioisotopic labels.

13. A method for diagnosing tumorigenicity comprising: measuring the level of GP88 protein in a first biological fluid sample taken from a patient; measuring the level of GP88 protein in a second biological fluid sample taken from said patient; and diagnosing tumorigenicity by determining whether the measured level of GP88 protein in said second biological fluid sample is higher than the level in said first biological fluid sample by an amount sufficient to indicate tumorigenicity.

14. The method of claim 13, wherein said biological fluid sample is selected from the group consisting of whole blood, plasma, serum, lymph, saliva, and urine.

15. The method of claim 13, wherein said second biological fluid samples is taken from said patient at least one week after said first biological fluid sample.

16. The method of claim 13, wherein said second biological fluid samples is taken from said patient at least one month after said first biological fluid sample.

17. The method of claim 13, wherein said concentration of GP88 is measured by an immunoassay.

18. The method of claim 17, wherein said immunoassay is selected from the group consisting of an enzyme linked immunoabsorbant assay and a radioimmunoassay.

19. A method of diagnosing tumorigenicity comprising measuring the level of GP88 in a biological fluid sample using an anti-GP88 antibody, and determining whether the level of GP88 in said biological fluid sample is sufficient to indicate tumorgenicity.

20. The method of claim 19, wherein a measured GP88 level of at least about 40 to about 50 nanograms per milliliter indicates tumorigenicity.

21. The method of claim 19, wherein said anti-GP88 antibody is produced from a hybridoma cell line selected from the group consisting of ATCC Accession Number PTA-5262, ATCC Accession Number PTA-5261, ATCC Accession Number PTA-5589, ATCC Accession Number PTA-5593, ATCC Accession Number PTA-5259, ATCC Accession Number PTA-5260, and ATCC Accession Number PTA-5291.

22. The method of claim 19, wherein said biological fluid sample is selected from the group consisting of whole blood, plasma, serum, lymph, saliva, and urine.

23. The method of claim 19, wherein said anti-GP88 antibody is used in an immunoassay.

24. The method of claim 23, wherein said immunoassay is an enzyme-linked immunoabsorbant assay.

25. The method of claim 23, wherein said immunoassay is a radioimmunoassay.

26. The method of claim 23, wherein said immunoassay is a Western blot.

27. A method of determining whether a patient is responding or responsive to anti-tumorigenic therapy, comprising measuring the concentration of GP88 in a biological fluid sample from a patient and determining whether the concentration of GP88 in said biological fluid sample is sufficient to indicate that said patient is not responding or responsive to anti-tumorigenic therapy.

28. The method of claim 27, wherein a GP88 concentration of at least about 100 to about 300 nanograms per milliliter is sufficient to indicate that said patient is not responding or responsive to anti-tumorigenic therapy.

29. The method of claim 27, wherein said anti-tumorigenic therapy is selected from group consisting of antiestrogen therapy, anti-GP88 antibody therapy, antisense therapy, chemotherapy, radiation treatment, and gene therapy.

30. The method of claim 27, wherein said GP88 concentration is measured using an anti-GP88 antibody or antibody fragment.

31. The method of claim 27, wherein said GP88 concentration is measured using a monoclonal anti-GP88 antibody or antibody fragment.

32. The method of claim 27, wherein said GP88 concentration is measured using a polyclonal anti-GP88 antibody or antibody fragment.

33. The method of claim 27, wherein said GP88 concentration is measured using more than one anti-GP88 antibody or antibody fragment.

34. The method of claim 30, wherein said anti-GP88 antibody or antibody fragment is unlabeled.

35. The method of claim 33, wherein said anti-GP88 antibody or antibody fragment is labeled with a label selected from the group consisting of enzymatic, fluorescent, and radioisotopic label.

36. The method of claim 35, wherein said enzymatic label is horseradish peroxidase.

37. The method of claim 35, wherein said radioisotopic label is $^{35}S$.

* * * * *

SEQUENCE LISTING

<160> NUMBER OF SEQ ID NOS: 17

<210> SEQ ID NO 1
<211> LENGTH: 2137
<212> TYPE: DNA
<213> ORGANISM: Mouse epithelin/granulin
<220> FEATURE:
<221> NAME/KEY: CDS
<222> LOCATION: (23)..(1789)
<223> OTHER INFORMATION: The sequence is identical to that of the
      published mouse granulin except for one nucleotide (T
      instead of G) at position 1071 of GP88 cDNA
      (position 1056 of mouse granulin).

<400> SEQUENCE: 1

-continued

| | |
|---|---|
| cggaccccga cgcagacaga cc atg tgg gtc ctg atg agc tgg ctg gcc ttc<br>                                       Met Trp Val Leu Met Ser Trp Leu Ala Phe<br>                                          1                 5                   10 | 52 |
| gcg gca ggg ctg gta gcc gga aca cag tgt cca gat ggg cag ttc tgc<br>Ala Ala Gly Leu Val Ala Gly Thr Gln Cys Pro Asp Gly Gln Phe Cys<br>               15                  20                 25 | 100 |
| cct gtt gcc tgc tgc ctt gac cag gga gga gcc aac tac agc tgc tgt<br>Pro Val Ala Cys Cys Leu Asp Gln Gly Gly Ala Asn Tyr Ser Cys Cys<br>          30                  35                 40 | 148 |
| aac cct ctt ctg gac aca tgg cct aga ata acg agc cat cat cta gat<br>Asn Pro Leu Leu Asp Thr Trp Pro Arg Ile Thr Ser His His Leu Asp<br>      45                50                 55 | 196 |
| ggc tcc tgc cag acc cat ggc cac tgt cct gct ggc tat tct tgt ctt<br>Gly Ser Cys Gln Thr His Gly His Cys Pro Ala Gly Tyr Ser Cys Leu<br> 60                  65                 70 | 244 |
| ctc act gtg tct ggg act tcc agc tgc tgc ccg ttc tct aag ggt gtg<br>Leu Thr Val Ser Gly Thr Ser Ser Cys Cys Pro Phe Ser Lys Gly Val<br> 75                  80                 85                 90 | 292 |
| tct tgt ggt gat ggc tac cac tgc tgc ccc cag ggc ttc cac tgt agt<br>Ser Cys Gly Asp Gly Tyr His Cys Cys Pro Gln Gly Phe His Cys Ser<br>                  95                100              105 | 340 |
| gca gat ggg aaa tcc tgc ttc cag atg tca gat aac ccc ttg ggt gct<br>Ala Asp Gly Lys Ser Cys Phe Gln Met Ser Asp Asn Pro Leu Gly Ala<br>        110                115              120 | 388 |
| gtc cag tgt cct ggg agc cag ttt gaa tgt cct gac tct gcc acc tgc<br>Val Gln Cys Pro Gly Ser Gln Phe Glu Cys Pro Asp Ser Ala Thr Cys<br>              125              130              135 | 436 |
| tgc att atg gtt gat ggt tcg tgg gga tgt tgt ccc atg ccc cag gcc<br>Cys Ile Met Val Asp Gly Ser Trp Gly Cys Cys Pro Met Pro Gln Ala<br>  140                  145              150 | 484 |
| tct tgc tgt gaa gac aga gtg cat tgc tgt ccc cat ggg gcc tcc tgt<br>Ser Cys Cys Glu Asp Arg Val His Cys Cys Pro His Gly Ala Ser Cys<br>155                  160              165              170 | 532 |
| gac ctg gtt cac aca cga tgc gtt tca ccc acg ggc acc cac acc cta<br>Asp Leu Val His Thr Arg Cys Val Ser Pro Thr Gly Thr His Thr Leu<br>              175              180              185 | 580 |
| cta aag aag ttc cct gca caa aag acc aac agc gca gtg tct ttg cct<br>Leu Lys Lys Phe Pro Ala Gln Lys Thr Asn Ser Ala Val Ser Leu Pro<br>        190                195              200 | 628 |
| ttt tct gtc gtg tgc cct gat gct aag acc cag tgt ccc gat gat tct<br>Phe Ser Val Val Cys Pro Asp Ala Lys Thr Gln Cys Pro Asp Asp Ser<br>              205              210              215 | 676 |
| acc tgc tgt gag cta ccc act ggg aag tat ggc tgc tgt cca atg ccc<br>Thr Cys Cys Glu Leu Pro Thr Gly Lys Tyr Gly Cys Cys Pro Met Pro<br>  220                  225              230 | 724 |
| aat gcc atc tgc tgt tcc gac cac ctg cac tgc tgc ccc cag gac act<br>Asn Ala Ile Cys Cys Ser Asp His Leu His Cys Cys Pro Gln Asp Thr<br>235                  240              245              250 | 772 |
| gta tgt gac ctg atc cag agt aag tgc cta tcc aag aac tac acc acg<br>Val Cys Asp Leu Ile Gln Ser Lys Cys Leu Ser Lys Asn Tyr Thr Thr<br>              255              260              265 | 820 |
| gat ctc ctg acc aag ctg cct gga tac cca gtg aag gag gtg aag tgc<br>Asp Leu Leu Thr Lys Leu Pro Gly Tyr Pro Val Lys Glu Val Lys Cys<br>        270                275              280 | 868 |
| gac atg gag gtg agc tgc cct gaa gga tat acc tgc tgc cgc ctc aac<br>Asp Met Glu Val Ser Cys Pro Glu Gly Tyr Thr Cys Cys Arg Leu Asn<br>  285                  290              295 | 916 |
| act ggg gcc tgg ggc tgc tgt cca ttt gcc aag gcc gtg tgt tgt gac<br>Thr Gly Ala Trp Gly Cys Cys Pro Phe Ala Lys Ala Val Cys Cys Asp | 964 |

-continued

```
            300                 305                 310
gat cac att cat tgc tgc ccg gca ggg ttt cag tgt cac aca gag aaa    1012
Asp His Ile His Cys Cys Pro Ala Gly Phe Gln Cys His Thr Glu Lys
315                 320                 325                 330 gga acc tgc gaa atg ggt atc ctc caa gta ggg tgg atg aag aag gtc    1060
Gly Thr Cys Glu Met Gly Ile Leu Gln Val Gly Trp Met Lys Lys Val
                335                 340                 345 ata gcc ccc ctc cgc ctg cca gac cca cag atc ttg aag agt gat aca    1108
Ile Ala Pro Leu Arg Leu Pro Asp Pro Gln Ile Leu Lys Ser Asp Thr
        350                 355                 360 cct tgt gat gac ttc act agg tgt cct aca aac aat acc tgc tgc aaa    1156
Pro Cys Asp Asp Phe Thr Arg Cys Pro Thr Asn Asn Thr Cys Cys Lys
    365                 370                 375 ctc aat tct ggg gac tgg ggc tgc tgt ccc atc cca gag gct gtc tgc    1204
Leu Asn Ser Gly Asp Trp Gly Cys Cys Pro Ile Pro Glu Ala Val Cys
380                 385                 390 tgc tca gac aac cag cat tgc tgc cct cag ggc ttc aca tgt ctg gct    1252
Cys Ser Asp Asn Gln His Cys Cys Pro Gln Gly Phe Thr Cys Leu Ala
395                 400                 405                 410 cag ggg tac tgt cag aag gga gac aca atg gtg gct ggc ctg gag aag    1300
Gln Gly Tyr Cys Gln Lys Gly Asp Thr Met Val Ala Gly Leu Glu Lys
                415                 420                 425 ata cct gcc cgc cag aca acc ccg ctc caa att gga gat atc ggt tgt    1348
Ile Pro Ala Arg Gln Thr Thr Pro Leu Gln Ile Gly Asp Ile Gly Cys
        430                 435                 440 gac cag cat acc agc tgc cca gta ggg caa acc tgc tgc cca agc ctc    1396
Asp Gln His Thr Ser Cys Pro Val Gly Gln Thr Cys Cys Pro Ser Leu
    445                 450                 455 aag gga agt tgg gcc tgc tgc cag ctg ccc cat gct gtg tgc tgt gag    1444
Lys Gly Ser Trp Ala Cys Cys Gln Leu Pro His Ala Val Cys Cys Glu
460                 465                 470 gac cgg cag cac tgt tgc ccg gcc ggg tac acc tgc aac gtg aag gcg    1492
Asp Arg Gln His Cys Cys Pro Ala Gly Tyr Thr Cys Asn Val Lys Ala
475                 480                 485                 490 agg acc tgt gag aag gat gtc gat ttt atc cag cct ccc gtg ctc ctg    1540
Arg Thr Cys Glu Lys Asp Val Asp Phe Ile Gln Pro Pro Val Leu Leu
                495                 500                 505 acc ctc ggc cct aag gtt ggg aat gtg gag tgt gga gaa ggg cat ttc    1588
Thr Leu Gly Pro Lys Val Gly Asn Val Glu Cys Gly Glu Gly His Phe
        510                 515                 520 tgc cat gat aac cag acc tgt tgt aaa gac agt gca gga gtc tgg gcc    1636
Cys His Asp Asn Gln Thr Cys Cys Lys Asp Ser Ala Gly Val Trp Ala
    525                 530                 535 tgt tgt ccc tac cta aag ggt gtc tgc tgt aga gat gga cgt cac tgt    1684
Cys Cys Pro Tyr Leu Lys Gly Val Cys Cys Arg Asp Gly Arg His Cys
540                 545                 550 tgc ccc ggt ggc ttc cac tgt tca gcc agg gga acc aag tgt ttg cga    1732
Cys Pro Gly Gly Phe His Cys Ser Ala Arg Gly Thr Lys Cys Leu Arg
555                 560                 565                 570 aag aag att cct cgc tgg gac atg ttt ttg agg gat ccg gtc cca aga    1780
Lys Lys Ile Pro Arg Trp Asp Met Phe Leu Arg Asp Pro Val Pro Arg
                575                 580                 585 ccg cta ctg taaggaaggg ctacagactt aaggaactcc acagtcctgg            1829
Pro Leu Leu gaaccctgtt ccgagggtac ccactactca ggcctcccta gcgcctcctc ccctaacgtc  1889
tccccggcct actcatcctg agtcacccta tcaccatggg aggtggagcc tcaaactaaa  1949
accttctttt atggaaagaa ggctctggcc aaaagccccg tatcaaactg ccatttcttc  2009
```

```
cggtttctgt ggaccttgtg gccaggtgct cttcccgagc cacaggtgtt ctgtgagctt      2069
gcttgtgtgt gtgtgcgcgt gtgcgtgtgt tgctccaata aagtttgtac gctttctgaa      2129
aaaaaaaa                                                               2137
```

<210> SEQ ID NO 2
<211> LENGTH: 589
<212> TYPE: PRT
<213> ORGANISM: Mouse epithelin/granulin

<400> SEQUENCE: 2

```
Met Trp Val Leu Met Ser Trp Leu Ala Phe Ala Ala Gly Leu Val Ala
 1               5                  10                  15

Gly Thr Gln Cys Pro Asp Gly Gln Phe Cys Pro Val Ala Cys Cys Leu
             20                  25                  30

Asp Gln Gly Gly Ala Asn Tyr Ser Cys Cys Asn Pro Leu Leu Asp Thr
         35                  40                  45

Trp Pro Arg Ile Thr Ser His His Leu Asp Gly Ser Cys Gln Thr His
     50                  55                  60

Gly His Cys Pro Ala Gly Tyr Ser Cys Leu Leu Thr Val Ser Gly Thr
 65                  70                  75                  80

Ser Ser Cys Cys Pro Phe Ser Lys Gly Val Ser Cys Gly Asp Gly Tyr
                 85                  90                  95

His Cys Cys Pro Gln Gly Phe His Cys Ser Ala Asp Gly Lys Ser Cys
            100                 105                 110

Phe Gln Met Ser Asp Asn Pro Leu Gly Ala Val Gln Cys Pro Gly Ser
        115                 120                 125

Gln Phe Glu Cys Pro Asp Ser Ala Thr Cys Cys Ile Met Val Asp Gly
    130                 135                 140

Ser Trp Gly Cys Cys Pro Met Pro Gln Ala Ser Cys Cys Glu Asp Arg
145                 150                 155                 160

Val His Cys Cys Pro His Gly Ala Ser Cys Asp Leu Val His Thr Arg
                165                 170                 175

Cys Val Ser Pro Thr Gly Thr His Thr Leu Leu Lys Lys Phe Pro Ala
            180                 185                 190

Gln Lys Thr Asn Ser Ala Val Ser Leu Pro Phe Ser Val Val Cys Pro
        195                 200                 205

Asp Ala Lys Thr Gln Cys Pro Asp Asp Ser Thr Cys Cys Glu Leu Pro
    210                 215                 220

Thr Gly Lys Tyr Gly Cys Cys Pro Met Pro Asn Ala Ile Cys Cys Ser
225                 230                 235                 240

Asp His Leu His Cys Cys Pro Gln Asp Thr Val Cys Asp Leu Ile Gln
                245                 250                 255

Ser Lys Cys Leu Ser Lys Asn Tyr Thr Thr Asp Leu Leu Thr Lys Leu
            260                 265                 270

Pro Gly Tyr Pro Val Lys Glu Val Lys Cys Asp Met Glu Val Ser Cys
        275                 280                 285

Pro Glu Gly Tyr Thr Cys Cys Arg Leu Asn Thr Gly Ala Trp Gly Cys
    290                 295                 300

Cys Pro Phe Ala Lys Ala Val Cys Cys Asp Asp His Ile His Cys Cys
305                 310                 315                 320

Pro Ala Gly Phe Gln Cys His Thr Glu Lys Gly Thr Cys Glu Met Gly
                325                 330                 335

Ile Leu Gln Val Gly Trp Met Lys Lys Val Ile Ala Pro Leu Arg Leu
            340                 345                 350
```

```
Pro Asp Pro Gln Ile Leu Lys Ser Asp Thr Pro Cys Asp Asp Phe Thr
        355                 360                 365

Arg Cys Pro Thr Asn Asn Thr Cys Cys Lys Leu Asn Ser Gly Asp Trp
    370                 375                 380

Gly Cys Cys Pro Ile Pro Glu Ala Val Cys Cys Ser Asp Asn Gln His
385                 390                 395                 400

Cys Cys Pro Gln Gly Phe Thr Cys Leu Ala Gln Gly Tyr Cys Gln Lys
                405                 410                 415

Gly Asp Thr Met Val Ala Gly Leu Glu Lys Ile Pro Ala Arg Gln Thr
            420                 425                 430

Thr Pro Leu Gln Ile Gly Asp Ile Gly Cys Asp Gln His Thr Ser Cys
        435                 440                 445

Pro Val Gly Gln Thr Cys Cys Pro Ser Leu Lys Gly Ser Trp Ala Cys
    450                 455                 460

Cys Gln Leu Pro His Ala Val Cys Cys Glu Asp Arg Gln His Cys Cys
465                 470                 475                 480

Pro Ala Gly Tyr Thr Cys Asn Val Lys Ala Arg Thr Cys Glu Lys Asp
                485                 490                 495

Val Asp Phe Ile Gln Pro Pro Val Leu Leu Thr Leu Gly Pro Lys Val
            500                 505                 510

Gly Asn Val Glu Cys Gly Glu Gly His Phe Cys His Asp Asn Gln Thr
        515                 520                 525

Cys Cys Lys Asp Ser Ala Gly Val Trp Ala Cys Cys Pro Tyr Leu Lys
    530                 535                 540

Gly Val Cys Cys Arg Asp Gly Arg His Cys Cys Pro Gly Gly Phe His
545                 550                 555                 560

Cys Ser Ala Arg Gly Thr Lys Cys Leu Arg Lys Lys Ile Pro Arg Trp
                565                 570                 575

Asp Met Phe Leu Arg Asp Pro Val Pro Arg Pro Leu Leu
            580                 585

<210> SEQ ID NO 3
<211> LENGTH: 19
<212> TYPE: PRT
<213> ORGANISM: mouse granulin
<220> FEATURE:
<221> NAME/KEY: PEPTIDE
<222> LOCATION: (1)..(19)
<223> OTHER INFORMATION: Internal peptide of mouse GP88 used to raise
      the antisera against the GP88 used in the immunoaffinity step.

<400> SEQUENCE: 3

Lys Lys Val Ile Ala Pro Arg Arg Leu Pro Asp Pro Gln Ile Leu Lys
1               5                   10                  15

Ser Asp Thr

<210> SEQ ID NO 4
<211> LENGTH: 12
<212> TYPE: PRT
<213> ORGANISM: mouse granulin
<220> FEATURE:
<221> NAME/KEY: PEPTIDE
<222> LOCATION: (1)..(12)
<223> OTHER INFORMATION: Internal peptide of mouse GP88 used to raise
      the antisera against the GP88 used in the immunoaffinity step.

<400> SEQUENCE: 4

Pro Asp Ala Lys Thr Gln Cys Pro Asp Asp Ser Thr
1               5                   10
```

<210> SEQ ID NO 5
<211> LENGTH: 14
<212> TYPE: PRT
<213> ORGANISM: mouse granulin
<220> FEATURE:
<221> NAME/KEY: PEPTIDE
<222> LOCATION: (1)..(14)
<223> OTHER INFORMATION: Internal peptide of mouse GP88 used to raise
      the antisera against the GP88 used in the immunoaffinity step.

<400> SEQUENCE: 5

Ser Ala Arg Gly Thr Lys Cys Leu Arg Lys Lys Ile Pro Arg
 1               5                  10

<210> SEQ ID NO 6
<211> LENGTH: 19
<212> TYPE: PRT
<213> ORGANISM: Human granulin
<220> FEATURE:
<221> NAME/KEY: PEPTIDE
<222> LOCATION: (1)..(19)
<223> OTHER INFORMATION: Internal peptide of human GP88 used to develop
      neutralizing anti-human GP88 monoclonal antibody.

<400> SEQUENCE: 6

Glu Lys Ala Pro Ala His Leu Ser Leu Pro Asp Pro Gln Ala Leu Lys
 1               5                  10                  15

Arg Asp Val

<210> SEQ ID NO 7
<211> LENGTH: 14
<212> TYPE: PRT
<213> ORGANISM: Human granulin
<220> FEATURE:
<221> NAME/KEY: PEPTIDE
<222> LOCATION: (1)..(14)
<223> OTHER INFORMATION: Internal peptide of human GP88 used to develop
      neutralizing anti-human GP88 monoclonal antibody.

<400> SEQUENCE: 7

Ala Arg Arg Gly Thr Lys Cys Leu Arg Arg Glu Ala Pro Arg
 1               5                  10

<210> SEQ ID NO 8
<211> LENGTH: 24
<212> TYPE: DNA
<213> ORGANISM: mammalian
<220> FEATURE:
<221> NAME/KEY: primer
<222> LOCATION: (1)..(24)
<223> OTHER INFORMATION: Internal peptide of CMV promoter used as PCR
      primer.

<400> SEQUENCE: 8
cctacttggc agtacatcta cgta                                          24

<210> SEQ ID NO 9
<211> LENGTH: 27
<212> TYPE: DNA
<213> ORGANISM: mammalian
<220> FEATURE:
<221> NAME/KEY: primer
<222> LOCATION: (1)..(27)
<223> OTHER INFORMATION: GP88 cDNA start codon used as oligonucleotide
      PCR primer.

<400> SEQUENCE: 9
cgagaattca ggcagaccat gtgggtc                                              27

<210> SEQ ID NO 10
<211> LENGTH: 27
<212> TYPE: DNA
<213> ORGANISM: mammalian
<220> FEATURE:
<221> NAME/KEY: primer
<222> LOCATION: (1)..(27)
<223> OTHER INFORMATION: Antisense primer oligonucleotide primer

<400> SEQUENCE: 10
cgagaattca ggcagaccat gtgggtc                                              27

<210> SEQ ID NO 11
<211> LENGTH: 23
<212> TYPE: DNA
<213> ORGANISM: mammalian
<220> FEATURE:
<221> NAME/KEY: primer
<222> LOCATION: (1)..(23)
<223> OTHER INFORMATION: Antisense primer oligonucleotide primer

<400> SEQUENCE: 11
ctgacggttc actaaacgag ctc                                                  23

<210> SEQ ID NO 12
<211> LENGTH: 25
<212> TYPE: DNA
<213> ORGANISM: mammalian
<220> FEATURE:
<221> NAME/KEY: primer
<222> LOCATION: (1)..(25)
<223> OTHER INFORMATION: primer

<400> SEQUENCE: 12
ggatccacgg agttgttacc tgatc                                                25

<210> SEQ ID NO 13
<211> LENGTH: 25
<212> TYPE: DNA
<213> ORGANISM: mammalian
<220> FEATURE:
<221> NAME/KEY: primer
<222> LOCATION: (1)..(25)
<223> OTHER INFORMATION: oligonucleotide PCR primer

<400> SEQUENCE: 13
gaattcgcag gcagaccatg tggac                                                25

<210> SEQ ID NO 14
<211> LENGTH: 21
<212> TYPE: DNA
<213> ORGANISM: mammalian
<220> FEATURE:
<221> NAME/KEY: primer
<222> LOCATION: (1)..(21)
<223> OTHER INFORMATION: Antisense oligonucleotide to human GP88

<400> SEQUENCE: 14
gggtccacat ggtctgcctg c                                                    21

<210> SEQ ID NO 15
<211> LENGTH: 24
<212> TYPE: DNA
<213> ORGANISM: mammalian
<220> FEATURE:
<221> NAME/KEY: primer -continued
<222> LOCATION: (1)..(24)
<223> OTHER INFORMATION: Antisense oligonucleotide to human GP88

<400> SEQUENCE: 15
gccaccagcc ctgctgttaa ggcc                                              24

<210> SEQ ID NO 16
<211> LENGTH: 2095
<212> TYPE: DNA
<213> ORGANISM: Human GP88 cDNA
<220> FEATURE:
<221> NAME/KEY: CDS
<222> LOCATION: (13)..(1791)
<223> OTHER INFORMATION: Nucleotide sequence of human granulin/epithelin
      precursor (human GP88). Human Granulin Genebank
      M75161.

<400> SEQUENCE: 16

```
cgcaggcaga cc atg tgg acc ctg gtg agc tgg gtg gcc tta aca gca ggg      51
              Met Trp Thr Leu Val Ser Trp Val Ala Leu Thr Ala Gly
                1               5                  10 ctg gtg gct gga acg cgg tgc cca gat ggt cag ttc tgc cct gtg gcc        99
Leu Val Ala Gly Thr Arg Cys Pro Asp Gly Gln Phe Cys Pro Val Ala
    15                  20                  25 tgc tgc ctg gac ccc gga gga gcc agc tac agc tgc tgc cgt ccc ctt       147
Cys Cys Leu Asp Pro Gly Gly Ala Ser Tyr Ser Cys Cys Arg Pro Leu
30                  35                  40                  45 ctg gac aaa tgg ccc aca aca ctg agc agg cat ctg ggt ggc ccc tgc       195
Leu Asp Lys Trp Pro Thr Thr Leu Ser Arg His Leu Gly Gly Pro Cys
                50                  55                  60 cag gtt gat gcc cac tgc tct gcc ggc cac tcc tgc atc ttt acc gtc       243
Gln Val Asp Ala His Cys Ser Ala Gly His Ser Cys Ile Phe Thr Val
            65                  70                  75 tca ggg act tcc agt tgc tgc ccc ttc cca gag gcc gtg gca tgc ggg       291
Ser Gly Thr Ser Ser Cys Cys Pro Phe Pro Glu Ala Val Ala Cys Gly
        80                  85                  90 gat ggc cat cac tgc tgc cca cgg ggc ttc cac tgc agt gca gac ggg       339
Asp Gly His His Cys Cys Pro Arg Gly Phe His Cys Ser Ala Asp Gly
    95                  100                 105 cga tcc tgc ttc caa aga tca ggt aac aac tcc gtg ggt gcc atc cag       387
Arg Ser Cys Phe Gln Arg Ser Gly Asn Asn Ser Val Gly Ala Ile Gln
110                 115                 120                 125 tgc cct gat agt cag ttc gaa tgc ccg gac ttc tcc acg tgc tgt gtt       435
Cys Pro Asp Ser Gln Phe Glu Cys Pro Asp Phe Ser Thr Cys Cys Val
                130                 135                 140 atg gtc gat ggc tcc tgg ggg tgc tgc ccc atg ccc cag gct tcc tgc       483
Met Val Asp Gly Ser Trp Gly Cys Cys Pro Met Pro Gln Ala Ser Cys
            145                 150                 155 tgt gaa gac agg gtg cac tgc tgt ccg cac ggt gcc ttc tgc gac ctg       531
Cys Glu Asp Arg Val His Cys Cys Pro His Gly Ala Phe Cys Asp Leu
        160                 165                 170 gtt cac acc cgc tgc atc aca ccc acg ggc acc cac ccc ctg gca aag       579
Val His Thr Arg Cys Ile Thr Pro Thr Gly Thr His Pro Leu Ala Lys
    175                 180                 185 aag ctc cct gcc cag agg act aac agg gca gtg gcc ttg tcc agc tcg       627
Lys Leu Pro Ala Gln Arg Thr Asn Arg Ala Val Ala Leu Ser Ser Ser
190                 195                 200                 205 gtc atg tgt ccg gac gca cgg tcc cgg tgc cct gat ggt tct acc tgc       675
Val Met Cys Pro Asp Ala Arg Ser Arg Cys Pro Asp Gly Ser Thr Cys
                210                 215                 220 tgt gag ctg ccc agt ggg aag tat ggc tgc tgc cca atg ccc aac gcc       723
Cys Glu Leu Pro Ser Gly Lys Tyr Gly Cys Cys Pro Met Pro Asn Ala
```

-continued

```
                    225                 230                 235
acc tgc tgc tcc gat cac ctg cac tgc ccc caa gac act gtg tgt        771
Thr Cys Cys Ser Asp His Leu His Cys Cys Pro Gln Asp Thr Val Cys
        240                 245                 250 gac ctg atc cag agt aag tgc ctc tcc aag gag aac gct acc acg gac    819
Asp Leu Ile Gln Ser Lys Cys Leu Ser Lys Glu Asn Ala Thr Thr Asp
255                 260                 265 ctc ctc act aag ctg cct gcg cac aca gtg ggc gat gtg aaa tgt gac    867
Leu Leu Thr Lys Leu Pro Ala His Thr Val Gly Asp Val Lys Cys Asp
270                 275                 280                 285 atg gag gtg agc tgc cca gat ggc tat acc tgc tgc cgt cta cag tcg   915
Met Glu Val Ser Cys Pro Asp Gly Tyr Thr Cys Cys Arg Leu Gln Ser
            290                 295                 300 ggg gcc tgg ggc tgc tgc cct ttt acc cag gct gtg tgc tgt gag gac    963
Gly Ala Trp Gly Cys Cys Pro Phe Thr Gln Ala Val Cys Cys Glu Asp
        305                 310                 315 cac ata cac tgc tgt ccc gcg ggg ttt acg tgt gac acg cag aag ggt    1011
His Ile His Cys Cys Pro Ala Gly Phe Thr Cys Asp Thr Gln Lys Gly
    320                 325                 330 acc tgt gaa cag ggg ccc cac cag gtg ccc tgg atg gag aag gcc cca    1059
Thr Cys Glu Gln Gly Pro His Gln Val Pro Trp Met Glu Lys Ala Pro
335                 340                 345 gct cac ctc agc ctg cca gac cca caa gcc ttg aag aga gat gtc ccc    1107
Ala His Leu Ser Leu Pro Asp Pro Gln Ala Leu Lys Arg Asp Val Pro
350                 355                 360                 365 tgt gat aat gtc agc agc tgt ccc tcc tcc gat acc tgc tgc caa ctc    1155
Cys Asp Asn Val Ser Ser Cys Pro Ser Ser Asp Thr Cys Cys Gln Leu
            370                 375                 380 acg tct ggg gag tgg ggc tgc tgt cca atc cca gag gct gtc tgc tgc    1203
Thr Ser Gly Glu Trp Gly Cys Cys Pro Ile Pro Glu Ala Val Cys Cys
        385                 390                 395 tcg gac cac cag cac tgc tgc ccc cag cga tac acg tgt gta gct gag    1251
Ser Asp His Gln His Cys Cys Pro Gln Arg Tyr Thr Cys Val Ala Glu
    400                 405                 410 ggg cag tgt cag cga gga agc gag atc gtg gct gga ctg gag aag atg    1299
Gly Gln Cys Gln Arg Gly Ser Glu Ile Val Ala Gly Leu Glu Lys Met
415                 420                 425 cct gcc cgc cgc ggt tcc tta tcc cac ccc aga gac atc ggc tgt gac    1347
Pro Ala Arg Arg Gly Ser Leu Ser His Pro Arg Asp Ile Gly Cys Asp
430                 435                 440                 445 cag cac acc agc tgc ccg gtg ggc gga acc tgc tgc ccg agc cag ggt    1395
Gln His Thr Ser Cys Pro Val Gly Gly Thr Cys Cys Pro Ser Gln Gly
            450                 455                 460 ggg agc tgg gcc tgc tgc cag ttg ccc cat gct gtg tgc tgc gag gat    1443
Gly Ser Trp Ala Cys Cys Gln Leu Pro His Ala Val Cys Cys Glu Asp
        465                 470                 475 cgc cag cac tgc tgc ccg gct ggc tac acc tgc aac gtg aag gct cga    1491
Arg Gln His Cys Cys Pro Ala Gly Tyr Thr Cys Asn Val Lys Ala Arg
    480                 485                 490 tcc tgc gag aag gaa gtg gtc tct gcc cag cct gcc acc ttc ctg gcc    1539
Ser Cys Glu Lys Glu Val Val Ser Ala Gln Pro Ala Thr Phe Leu Ala
495                 500                 505 cgt agc cct cac gtg ggt gtg aag gac gtg gag tgt ggg gaa gga cac    1587
Arg Ser Pro His Val Gly Val Lys Asp Val Glu Cys Gly Glu Gly His
510                 515                 520                 525 ttc tgc cat gat aac cag acc tgc tgc cga gac aac cga cag ggc tgg    1635
Phe Cys His Asp Asn Gln Thr Cys Cys Arg Asp Asn Arg Gln Gly Trp
            530                 535                 540 gcc tgc tgt ccc tac gcc cag ggc gtc tgt tgt gct gat cgg cgc cac    1683
```

```
                  Ala Cys Cys Pro Tyr Ala Gln Gly Val Cys Cys Ala Asp Arg Arg His
                          545                 550                 555 tgc tgt cct gct ggc ttc cgc tgc gca cgc agg ggt acc aag tgt ttg          1731
Cys Cys Pro Ala Gly Phe Arg Cys Ala Arg Arg Gly Thr Lys Cys Leu
        560                 565                 570 cgc agg gag gcc ccg cgc tgg gac gcc cct ttg agg gac cca gcc ttg          1779
Arg Arg Glu Ala Pro Arg Trp Asp Ala Pro Leu Arg Asp Pro Ala Leu
    575                 580                 585 aga cag ctg ctg tgagggacag tactgaagac tctgcagccc tcgggacccc              1831
Arg Gln Leu Leu
590 actcggaggg tgccctctgc tcaggcctcc ctagcacctc ccctaacca aattctccct         1891 ggacccatt ctgagctccc catcaccatg ggaggtgggg cctcaatcta aggcccttcc         1951 ctgtcagaag ggggttgagg caaaagccca ttacaagctg ccatcccctc cccgtttcag        2011 tggaccctgt ggccaggtgc ttttccctat ccacaggggt gtttgtgtgt tgggtgtgct       2071 ttcaataaag tttgtcactt tctt                                               2095

<210> SEQ ID NO 17
<211> LENGTH: 593
<212> TYPE: PRT
<213> ORGANISM: Human GP88 cDNA

<400> SEQUENCE: 17

Met Trp Thr Leu Val Ser Trp Val Ala Leu Thr Ala Gly Leu Val Ala
  1               5                  10                  15

Gly Thr Arg Cys Pro Asp Gly Gln Phe Cys Pro Val Ala Cys Cys Leu
                 20                  25                  30

Asp Pro Gly Gly Ala Ser Tyr Ser Cys Cys Arg Pro Leu Leu Asp Lys
             35                  40                  45

Trp Pro Thr Thr Leu Ser Arg His Leu Gly Gly Pro Cys Gln Val Asp
         50                  55                  60

Ala His Cys Ser Ala Gly His Ser Cys Ile Phe Thr Val Ser Gly Thr
 65                  70                  75                  80

Ser Ser Cys Cys Pro Phe Pro Glu Ala Val Ala Cys Gly Asp Gly His
                 85                  90                  95

His Cys Cys Pro Arg Gly Phe His Cys Ser Ala Asp Gly Arg Ser Cys
                100                 105                 110

Phe Gln Arg Ser Gly Asn Asn Ser Val Gly Ala Ile Gln Cys Pro Asp
            115                 120                 125

Ser Gln Phe Glu Cys Pro Asp Phe Ser Thr Cys Cys Val Met Val Asp
        130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
```

-continued

```
                245                 250                 255
Gln Ser Lys Cys Leu Ser Lys Glu Asn Ala Thr Thr Asp Leu Leu Thr
                260                 265                 270
Lys Leu Pro Ala His Thr Val Gly Asp Val Lys Cys Asp Met Glu Val
                275                 280                 285
Ser Cys Pro Asp Gly Tyr Thr Cys Cys Arg Leu Gln Ser Gly Ala Trp
                290                 295                 300
Gly Cys Cys Pro Phe Thr Gln Ala Val Cys Cys Glu Asp His Ile His
305                 310                 315                 320
Cys Cys Pro Ala Gly Phe Thr Cys Asp Thr Gln Lys Gly Thr Cys Glu
                325                 330                 335
Gln Gly Pro His Gln Val Pro Trp Met Glu Lys Ala Pro Ala His Leu
                340                 345                 350
Ser Leu Pro Asp Pro Gln Ala Leu Lys Arg Asp Val Pro Cys Asp Asn
                355                 360                 365
Val Ser Ser Cys Pro Ser Ser Asp Thr Cys Cys Gln Leu Thr Ser Gly
                370                 375                 380
Glu Trp Gly Cys Cys Pro Ile Pro Glu Ala Val Cys Cys Ser Asp His
385                 390                 395                 400
Gln His Cys Cys Pro Gln Arg Tyr Thr Cys Val Ala Glu Gly Gln Cys
                405                 410                 415
Gln Arg Gly Ser Glu Ile Val Ala Gly Leu Glu Lys Met Pro Ala Arg
                420                 425                 430
Arg Gly Ser Leu Ser His Pro Arg Asp Ile Gly Cys Asp Gln His Thr
                435                 440                 445
Ser Cys Pro Val Gly Gly Thr Cys Cys Pro Ser Gln Gly Gly Ser Trp
                450                 455                 460
Ala Cys Cys Gln Leu Pro His Ala Val Cys Cys Glu Asp Arg Gln His
465                 470                 475                 480
Cys Cys Pro Ala Gly Tyr Thr Cys Asn Val Lys Ala Arg Ser Cys Glu
                485                 490                 495
Lys Glu Val Val Ser Ala Gln Pro Ala Thr Phe Leu Ala Arg Ser Pro
                500                 505                 510
His Val Gly Val Lys Asp Val Glu Cys Gly Glu Gly His Phe Cys His
                515                 520                 525
Asp Asn Gln Thr Cys Cys Arg Asp Asn Arg Gln Gly Trp Ala Cys Cys
                530                 535                 540
Pro Tyr Ala Gln Gly Val Cys Cys Ala Asp Arg Arg His Cys Cys Pro
545                 550                 555                 560
Ala Gly Phe Arg Cys Ala Arg Arg Gly Thr Lys Cys Leu Arg Arg Glu
                565                 570                 575
Ala Pro Arg Trp Asp Ala Pro Leu Arg Asp Pro Ala Leu Arg Gln Leu
                580                 585                 590
Leu
```